US008825508B2

(12) United States Patent
Nilsson

(10) Patent No.: US 8,825,508 B2
(45) Date of Patent: Sep. 2, 2014

(54) METHOD AND APPARATUS FOR AUTOMATED STAFF ASSIGNMENT

(75) Inventor: Agneta Nilsson, Pixbo (SE)

(73) Assignee: Ascom Tateco AB, Gothenburg (SE)

( * ) Notice: Subject to any disclaimer, the term of this patent is extended or adjusted under 35 U.S.C. 154(b) by 1930 days.

(21) Appl. No.: 11/415,118

(22) Filed: May 2, 2006

(65) Prior Publication Data
US 2007/0288285 A1 Dec. 13, 2007

(51) Int. Cl.
G06Q 10/00 (2012.01)

(52) U.S. Cl.
USPC .......................................... 705/7.17; 705/7.13

(58) Field of Classification Search
CPC ....................................................... G06Q 10/06
USPC .................................................. 705/7.17, 7.13
See application file for complete search history.

(56) References Cited

U.S. PATENT DOCUMENTS

| 5,530,861 | A | * | 6/1996 | Diamant et al. | 705/8 |
| 5,576,952 | A | | 11/1996 | Stutman et al. | |
| 5,867,596 | A | * | 2/1999 | Kano et al. | 382/203 |
| 5,942,986 | A | | 8/1999 | Shabot et al. | |
| 5,974,392 | A | * | 10/1999 | Endo | 705/8 |
| 6,057,782 | A | | 5/2000 | Koenig | |
| 6,345,260 | B1 | | 2/2002 | Cummings, Jr. et al. | |
| 6,415,277 | B1 | * | 7/2002 | Klatt et al. | 1/1 |
| 6,801,780 | B1 | | 10/2004 | Foladare et al. | |
| 6,889,196 | B1 | * | 5/2005 | Clark | 705/9 |
| 2002/0103691 | A1 | | 8/2002 | Smith | |
| 2002/0123921 | A1 | | 9/2002 | Frazier | |
| 2002/0138328 | A1 | * | 9/2002 | Arning et al. | 705/9 |
| 2003/0033308 | A1 | * | 2/2003 | Patel et al. | 707/10 |
| 2003/0045958 | A1 | * | 3/2003 | Brandt et al. | 700/101 |
| 2003/0061089 | A1 | | 3/2003 | Weaver | |
| 2003/0110069 | A1 | * | 6/2003 | Nishizono | 705/8 |
| 2003/0220829 | A1 | | 11/2003 | Seally | |
| 2004/0220847 | A1 | * | 11/2004 | Ogushi et al. | 705/9 |
| 2004/0225535 | A1 | * | 11/2004 | Bond et al. | 705/4 |
| 2004/0267595 | A1 | * | 12/2004 | Woodings et al. | 705/9 |
| 2005/0066002 | A1 | * | 3/2005 | Teres et al. | 709/204 |
| 2005/0209902 | A1 | * | 9/2005 | Iwasaki et al. | 705/8 |
| 2005/0254712 | A1 | * | 11/2005 | Lindeman | 382/224 |

(Continued)

FOREIGN PATENT DOCUMENTS

EP 1610253 A1 * 12/2005

OTHER PUBLICATIONS

"Specification and Implementation of Exceptions in Workflow Management System", by Fabio Casati et al., ACM Transactions on Database System, vol. 24, No. 3, Sep. 1999.*

(Continued)

Primary Examiner — Justin M Pats
Assistant Examiner — Pan Choy
(74) Attorney, Agent, or Firm — Birch, Stewart, Kolasch & Birch, LLP

(57) ABSTRACT

A method and an apparatus perform automatic assignment in an environment. The apparatus according to one embodiment comprises an event handler for extracting event elements from reports in the environment; an assignment handler for assigning information to the reports, the assignment handler assigning information to the reports by assigning events to the reports using the event elements of the reports, and assigning staff of the environment to the events; and an action handler for generating actions for the events and sending the actions to the assigned staff.

30 Claims, 17 Drawing Sheets

(56) References Cited

U.S. PATENT DOCUMENTS

| | | | | |
|---|---|---|---|---|
| 2006/0111939 | A1* | 5/2006 | Bixler et al. | 705/2 |
| 2006/0224750 | A1* | 10/2006 | Davies et al. | 709/229 |
| 2007/0067200 | A1* | 3/2007 | Patel | 705/9 |
| 2007/0067772 | A1* | 3/2007 | Bustamante | 718/100 |
| 2007/0201673 | A1* | 8/2007 | Annadata et al. | 379/265.01 |
| 2008/0042807 | A1* | 2/2008 | Park et al. | 340/10.3 |

OTHER PUBLICATIONS

"An Evaluation of Methodological Issues in Workflow Management", by Anastasia Sotnikova, Department of Computer Engineering and Information Science and the Institute of Engineering and Science of Bilikent University, Aug. 1998.*

"Workflow Based Application", by F. Leymann and D. Roller, IBM System Journal, vol. 36, No. 1, 1997.*

"Specification and Implementation of Exceptions in Workflow Management System", by Fabio Casati et al., ACM Transactions on Database System, vol. 24, No. 3, Sep. 1999, pp. 405-451.*

"An Evaluation of Methodological Issues in Workflow Management", by Anastasia Sotnikova, Department of Computer Engineering and Information Science and the Institute of Engineering and Science of Bilikent University, Aug. 1998.*

"Conceptual Design and Implementation of a Graphical Workflow-Modeling Editor in the Context of Distributed Groupware-Databases", by Marcus Ott, University of Paderborn Faculty of Business Studies, Germany, May 1994.*

"Workforce Planning: An Overview for Discussion", Mercer Human Resource Consulting LLC, Dec. 2005.*

"Multi-Criteria Task Assignment in Workflow Management Systems", by Minxin Shen et al., Institute of Information Management, National Chiao Tung University, Taiwan; Proceedings of the 36th Hawaii International Conference on System Sciences; The computer Society, IEEE 2002.*

"Socially and Individually Optimal Routing of Stochastic Jobs in Parallel Processor System", by Susan H. Xu, The Pennsylvania State University; Operations Research Society of America; vol. 40, No. 2, Mar.-Apr. 1992.*

"A Large-Scale Relation and Event Extraction System", by C. Aone, M. Ramos-Santacruz; In: 6th Applied Natural Language Processing Conference, 2000; pp. 76-83.*

"Automatically Constructing a Dictionary for Information Extraction Tasks", by Ellen Riloffl, Proceedings of the Eleventh National Conference on Artificial Intelligence, 1993, AAAI Press/MIT Press, p. 811-816.*

"Constraint-Based Event Recognition for Information Extraction", by Jeremy Crowe, Department of Artificial Intelligence, Edinburgh University, Edinburgh, UK, 1997.*

"Email Event Extraction and Interpretation", by Keith Ito, Stanford University, Jun. 5, 2003.*

"Combining Techniques for Event Extraction in Summary Reports", by Nancy McCracken et al., 2006, American Association for Artifical Intelligence.*

"Staff Scheduling and Rostering: A review of Applications, methods and models", by A.T. Ernst et al., CSIRO Mathematical and Information Sciences, Private Bag 10, Clayton South MDC, Clayton, Vic. 3169, Australia, European Journal of Operational Research 153, 2004.*

"Assignment and Scheduling Communicating Periodic Tasks in Distributed Real-Time Systems", by Dar-Tzen Peng et al., IEEE Transactions on Software Engineering, vol. 23, No. 12, Dec. 1997.*

* cited by examiner

FIG. 13A

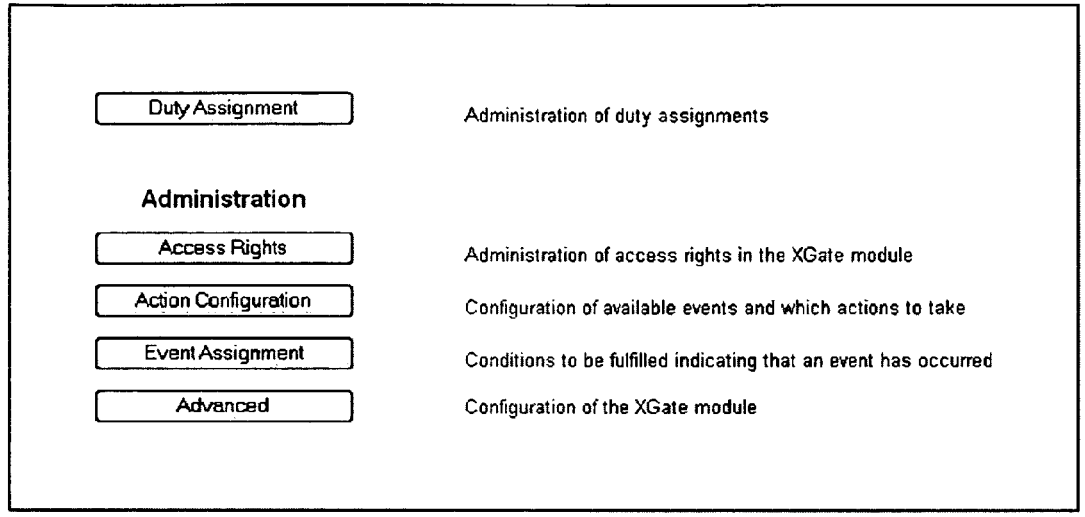

FIG. 13B

XGate

| Basic | Advanced |

Basic Setup
- Basic Setup
- Set Language
- Backup/Restore

User Administration

Access Rights Administration — Set up access rights for the Unite User Teams

Action Handling

Action Configuration — Set up of actions for the event that occurred. Define what to transmit and success and failure conditions

Assignments

Event Assignment — Set up which Event Elements that correspond to a certain Event
Duty Assignment — Set up addressees for the actions

Input Data Conversions

Translation Tables

FIG. 13F

METHOD AND APPARATUS FOR AUTOMATED STAFF ASSIGNMENT

BACKGROUND OF THE INVENTION

1. Field of the Invention

The present invention relates to assignment systems for complex environments, and more particularly to a method and apparatus providing automated staff assignment in hospital and industrial environments.

2. Description of the Related Art

Complex environments such as hospitals and industrial facilities typically include a large number of complex equipment, databases, staff, and patients or clients. Consequently, when an emergency occurs in a hospital or industrial facility, a lot of equipment needs attention, a multitude of databases need to be consulted, and a large number of staff personnel needs to be notified to address the emergency. The personnel assigned to take action in a given emergency is usually on the move somewhere in the hospital or industrial environment. Therefore, wireless communication means are essential for contacting the appropriate personnel within a short timeframe. The personnel that needs to address the emergency depends on the type of the emergency, the time of day, as well as other circumstances such as personnel attendance and competing tasks. Therefore, complex assignment and selection systems are needed to determine the correct identity of personnel to be notified during emergency alerts. Such complex functions can be best performed by an automated assignment system.

In complex environments such as hospitals and industrial facilities, alerts are generated from a wide variety of equipment. An automated assignment system needs to be able to receive alerts from various kinds of systems, interpret many different input protocols, and transfer alerts to different messaging systems and devices. In an automated assignment system, changing the assignments configuration for various emergency alerts needs to be a simple task for the authorized personnel. The efficiency and speed of operation of an automatic assignment system directly impacts operations in a hospital or industrial facility, and can save lives.

Existing staff assignment systems encounter significant challenges when used in a complex environment such as a hospital or an industrial facility. Response turn-around time is often an issue, due to the large number of formats and protocols in which emergency alerts are transmitted. Automation of assignment systems is hindered because of inability to process various message formats. Moreover, inefficient staff assignments are often made because of difficulty to quickly select the escalation path appropriate for the alarm type, time of day, etc.

A few publications have studied assignment systems for hospital environments. One such system is described in U.S. Pat. No. 6,801,780 B1 entitled "Method and Apparatus for Providing Intelligent Emergency Paging." With the method described in this work, however, no processing and assignment for messages other than pages are described. Moreover, the assignment system described in the above work is not configured to interface with external automated systems and extract information automatically from incoming messages.

Another technique is described in U.S. Pat. No. 5,942,986 entitled "System and Method for Automatic Critical Event Notification." The technique described in this work, however, is limited to pagers and pager networks with PIN protected access, and can handle only a limited range of message alert formats. Moreover, the message alerts addressed in the above work represent only one type of emergency (a medical emergency). No alternative escalation paths and plans are provided in case pages are not received by the designated physicians and nurses.

A disclosed embodiment of the application addresses these and other issues by utilizing an automated staff assignment method and apparatus. The automated staff assignment method and apparatus can understand and process message alerts in a variety of formats and sent through a variety of protocols, and can transfer response action messages through a variety of protocols. The automated staff assignment method and apparatus can perform efficient staff assignment under multiple constraints and in real-time, and can sort and search through a large amount of information to determine the personnel trained and available to address a given emergency.

SUMMARY OF THE INVENTION

The present invention is directed to a method and an apparatus for automated assignment in an environment. According to a first aspect of the present invention, an apparatus for automated staff assignment in an environment comprises: an event handler for extracting event elements from reports in the environment; an assignment handler for assigning information to the reports, the assignment handler assigning information to the reports by assigning events to the reports using the event elements of the reports, and assigning staff of the environment to the events; and an action handler for generating actions for the events and sending the actions to the assigned staff.

According to a second aspect of the present invention, an apparatus for automated assignment in an environment comprises: an event handler for extracting event elements from reports in the environment; an assignment handler for assigning information to the reports, the assignment handler assigning information to the reports by assigning events to the reports using the event elements of the reports, and assigning systems of the environment to the events; and an action handler for generating actions for the events and sending the actions to the assigned systems.

According to a third aspect of the present invention, a method of automatically assigning staff in an environment comprises: extracting event elements from reports in the environment; assigning information to the reports, the step of assigning information to the reports including assigning events to the reports using the event elements of the reports, and assigning staff of the environment to the events; generating actions for the events; and sending the actions to the assigned staff.

BRIEF DESCRIPTION OF THE DRAWINGS

Further aspects and advantages of the present invention will become apparent upon reading the following detailed description in conjunction with the accompanying drawings, in which:

FIG. 13A illustrates a start page for an exemplary implementation of an automated medical staff assignment system according to an embodiment of the present invention;

FIG. 13B illustrates a graphical interface for basic setup of an exemplary implementation of an automated medical staff assignment system according to an embodiment of the present invention;

FIG. 13F is a graphical interface for a duty assignment unit in an exemplary implementation of an automated medical staff assignment system according to an embodiment of the present invention.

DETAILED DESCRIPTION

Figure 1:
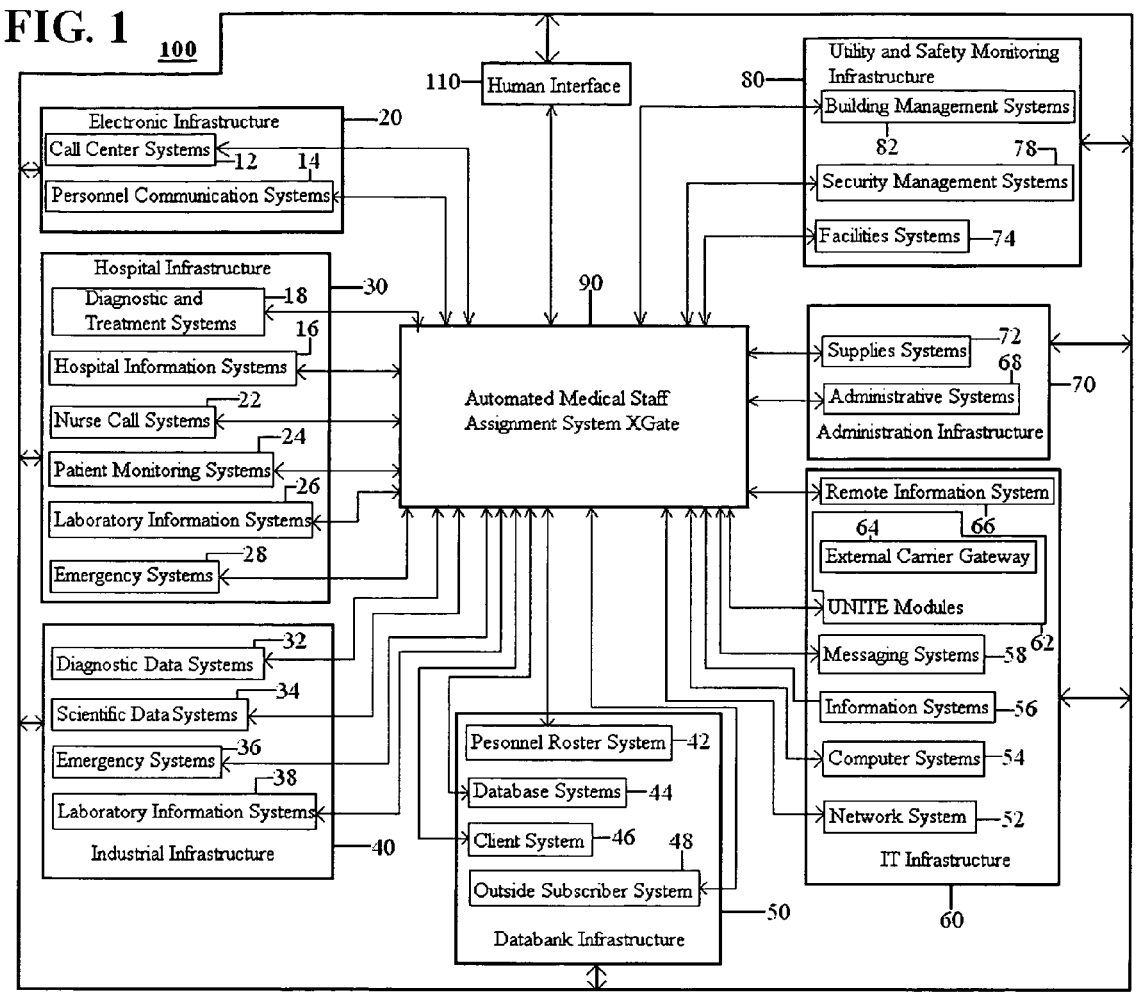
FIG. 1 is a general block diagram of a hospital environment including an automated medical staff assignment system according to an embodiment of the present invention.

Aspects of the invention are more specifically set forth in the accompanying description with reference to the appended figures. Although aspects of the present invention are described and illustrated in the context of a hospital environment, it should be recognized that principles of the present invention are not limited to such an environment. FIG. 1 is a general block diagram of a hospital environment 100 including an automated medical staff assignment system 90 according to an embodiment of the present invention. The automated medical staff assignment system 90 is also referenced to as "XGate" in the current application. Hospital environment 100 illustrated in FIG. 1 includes the following components: electronic infrastructure 20; hospital infrastructure 30; industrial infrastructure 40; databank infrastructure 50; IT infrastructure 60; administration infrastructure 70; utility and safety monitoring infrastructure 80; human interface 110; and automated medical staff assignment system (XGate) 90. Operations inside hospital environment 100 in FIG. 1 will become apparent from the following discussion.

Electronic infrastructure 20 includes call center systems 12 and personnel communication systems 14. Call center systems 12 include electrical, mechanical, as well as other types of systems used for receiving, recording and routing calls from inside and outside hospital environment 100. Call center systems 12 send message alerts received as calls, to XGate 90. Personnel communication systems 14 are devices used by hospital personnel to send and receive messages. Such devices include pagers, cell phones, PDAs, wireless receivers, antennas, two-way radios, walkie-talkies, etc. These devices can send message alerts to XGate 90.

Hospital infrastructure 30 includes the following components: diagnostic and treatment systems 18; hospital information systems 16; nurse call systems 22; patient monitoring systems 24; laboratory information systems 26; and emergency systems 28. Diagnostic and treatment systems 18 include devices used in diagnosing and treating ailments. Such devices include tomography systems, laser surgery systems, X-ray systems, etc. Diagnostic and treatment systems 18 send message alerts to XGate 90 about malfunctions of diagnostic and treatment systems. If the diagnostic and treatment systems 18 are connected to a network, diagnostic and treatment systems 18 also send messages about abnormal patient vital signs readings. Hospital information systems 16 include infrastructure that relays information about patients to hospital staff, such as file room systems and medical reference systems. Nurse call systems 22 include the electric and electronic infrastructure used by nursing staff, such as machines used to call for a nurse's attention, call boxes, office phone, headsets, buttons or strings located next to hospital beds, etc. Nurse call systems 22 also include central systems that collect patients' calls. Patient monitoring systems 24 include devices used for monitoring the state of patients, such as cardiac monitoring systems and computer interfaces monitoring real-time patient data. Laboratory information systems 26 include devices that analyze, record and store lab results, such as glucose level, weight and cholesterol measuring systems. Emergency systems 28 include hospital equipment used in emergency rooms, such as defibrillators and loud interphone systems.

Industrial infrastructure 40 includes the following components: diagnostic data systems 32; scientific data systems 34; emergency systems 36; and laboratory information systems 38. Industrial infrastructure 40 can be part of a research facility connected to a hospital. Alternatively, industrial infrastructure 40 can be part of an industrial environment or scientific facility unrelated to a medical establishment. Diagnostic data systems 32 include electric and mechanical systems such as voltmeters and thermocouples that monitor the functional status of research or industrial equipment. Scientific data systems 34 include research or industrial equipment such as particle accelerators or turbines present in a research or industrial environment. Emergency systems 36 include electrical or mechanical systems that monitor and report anomalous readings and functional states of research or industrial equipment. Laboratory information systems 38 include electrical and mechanical systems that contain information on specifications, data sheets, or defective parts of research or industrial equipment. Laboratory information systems 38 also include systems that record and keep scientific information related to results of scientific experiments performed in a research or industrial environment.

Databank infrastructure 50 includes the following components: personnel roster system 42; database systems 44; client system 46; and outside subscriber system 48. Personnel roster system 42 includes databanks with personnel names and background information, as well as responsibilities, skills, and attendance information. Database systems 44 include databases with factual information related to various facilities of hospital environment 100. Such information includes lists of hospital rooms, with sizes and current use, lists of medical equipment in various sections of hospital environment 100, etc. Client system 46 includes databases with names, personal, medical, and billing information of clients who use the services provided by hospital environment 100. Outside subscriber system 48 includes databases of persons or organizational entities that subscribe remotely to services provided by hospital environment 100.

IT infrastructure 60 includes the following components: remote information system 66; UNITE modules 62; messaging systems 58; information systems 56; computer systems 54; and network system 52. Remote information system 66 includes infrastructure that transmits information from a remote location. Such infrastructure may include, for example, wireless links transmitting health data of personnel at a remote location, through satellites. Computer systems 54 include servers and computers used in hospital environment 100. Information systems 56 include infrastructure used in computer systems 54, such as software systems and operation systems. Network system 52 includes devices that connect various parts of IT infrastructure 60, such as modems, routers and Internet cables. Messaging systems 58 include devices and software used to send or receive messages in IT infrastructure 60. Such devices and software include speakers, email servers, online talk applications, Internet phone software, etc.

UNITE modules 62 is an integrated messaging system launched by Ascom Wireless Solutions, to help organizations in manufacturing, power, energy and process industries improve efficiency and minimize problems associated with production disturbances and downtime. UNITE modules 62 consist of embedded computing servers with software applications. UNITE modules 62 allow staff in production, security, health, and safety roles to respond more quickly and efficiently to time-critical information, regardless of their location. UNITE modules 62 automatically convert messages from a variety of sources, such as message alarms on a production line or security device, into the format required by the communication devices the intended recipients are using, e.g. a cordless phone, a pager, a mobile phone, etc. Examples of applications included in UNITE modules 62 are TCP/IP Messaging systems NetPage and MailGate. NetPage provides access to the paging and telephone systems from local web-browsers. A user of NetPage simply enters the call or pager number and the text, presses "send", and a few seconds later the message reaches the recipient. MailGate is a system that sends notifications to pagers or cordless telephones when an awaited e-mail arrives. MailGate can also be used in conjunction with surveillance devices. UNITE modules 62 includes an external carrier gateway (ECG) 64. ECG 64 includes systems that allow messages to be delivered to external messaging systems located onsite or offsite. ECG 64 has the capability of converting UNITE messaging blocks to other standard protocols such as TAP (Telocator Alphanumeric Protocol), SNPP (Simple Network Paging Protocol) and ESPA. ESPA is a serial protocol intended for the interconnection of paging equipment with telephone exchanges systems or computer systems.

Administration infrastructure 70 includes the following components: supplies systems 72; and administrative systems 68. Supplies systems 72 include systems that store supplies and spare parts, and record the quantity and need for supplies and spare parts, such as log e-books, supply databases, and supply rooms with security systems. Administrative systems 68 include systems used by the administrative staff in hospital environment 100, such as admin lists, e-books, benefits database systems, etc.

Utility and safety monitoring infrastructure 80 includes the following components: building management systems 82; security management systems 78; and facilities systems 74. Building management systems 82 include systems that manage equipment and information related to the wellbeing of the buildings of hospital environment 100. Facilities systems 74 include electrical and mechanical systems of buildings of hospital environment 100, as well as electrical and mechanical systems that monitor and repair building systems. Electrical and mechanical systems included in facilities systems 74 are an electrical system, a fire system, a heating system, an AC system, etc. Security management systems 78 include equipment used for security purposes, such as surveillance cameras, remote controls, automatic locks, ID scanners, etc.

Human interface 110 includes personnel that work in and for hospital environment 100. Such personnel include nurses, physicians, technical staff, etc. Human interface 110 operates and monitors the systems and infrastructures of hospital environment 100.

Automated medical staff assignment system (XGate) 90 handles different types of protocols and receives message alerts from electronic infrastructure 20, hospital infrastructure 30, industrial infrastructure 40, databank infrastructure 50, IT infrastructure 60, administration infrastructure 70, utility and safety monitoring infrastructure 80, and human interface 110. XGate 90 responds to received message alerts by executing automated assignment of tasks. XGate 90 converts events to actions, executes task assignments, provides an assignment interface to offer the ability for users to assign recipients to events, etc. The responses of XGate 90 are sent back to the appropriate infrastructures of hospital environment 100, as well as to the relevant personnel from human interface 110. Assignments may be communicated directly to a person, or sent to that person through an infrastructure system of hospital environment 100. Assignments may also be addressed solely to machines included in infrastructure systems of hospital environment 100, in case such assignments include, for example, a request for an immediate automatic shutoff of an electrical system.

XGate 90 can be implemented for large-scale use in hospitals or industries connected to automated systems, thus coping with complex systems. One exemplary use of XGate 90 is for everyday use at a medical ward, assigning available staff to selected tasks based on medical need, as well as location and/or time-of-day. XGate 90 solves the need to allocate the right people to specific tasks, and to get messages through to them when their attention is required. The intended user could be, for example, the person responsible to plan the work at each specific hospital ward. XGate 90 can also ensure that the generated action requests reach their destination. For this purpose, XGate 90 can use a feedback mechanism to make sure that assignment actions requests have been received. Hence, XGate 90 may be set up to require confirmation on delivery, or user response. A user can have the option to acknowledge, accept or reject a message. A confirmatory system set up in XGate 90 can ensure that the assigned persons have done their job assigned for a given event. Advanced escalation chains may be set up to assign a task to a second person, when the first notified person is not available or declines to undertake the assigned task.

Figure 2:
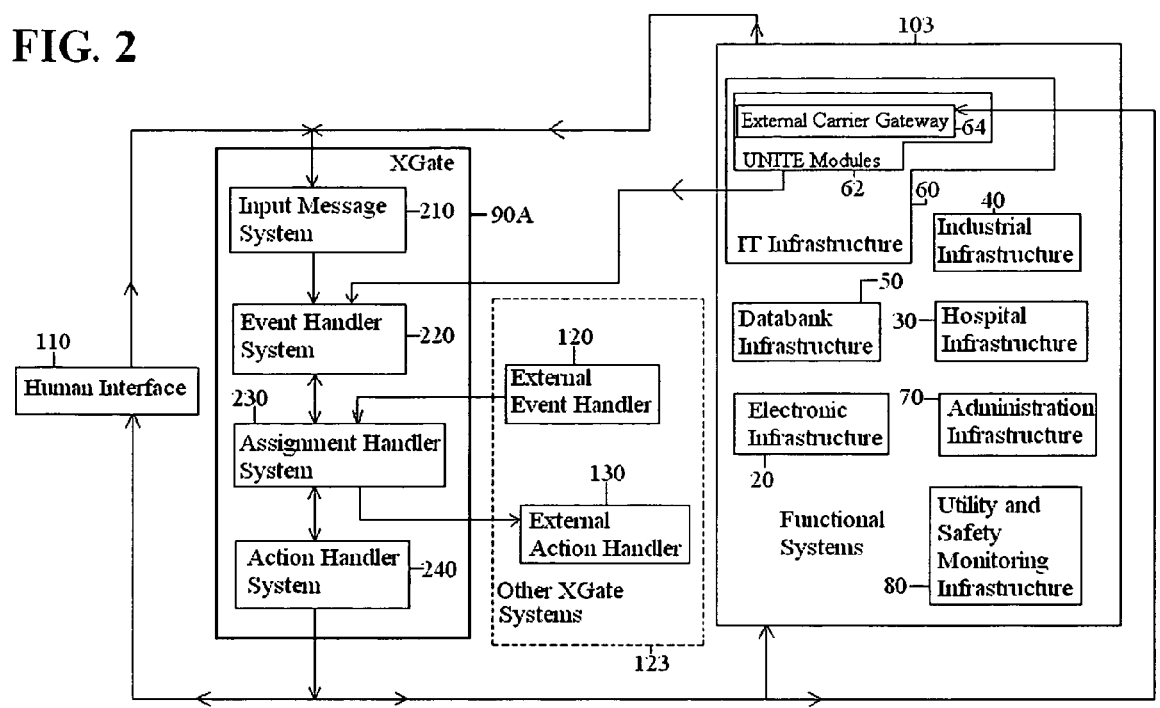
FIG. 2 is a functional block diagram of an automated medical staff assignment system according to an embodiment of the present invention.

FIG. 2 is a functional block diagram of an automated medical staff assignment (XGate) system 90A according to an embodiment of the present invention. XGate system 90A includes a plurality of functional modules as illustrated in FIG. 2: an input message system 210; an event handler system 220; an assignment handler system 230; and an action handler system 240. Although the functional modules included in XGate system 90A are shown as discrete elements, it should be recognized that the associated functions of the functional modules may be performed by one or more physical elements, such as a server or a network of servers or computers.

Input message system 210 receives message alerts from human interface 110 and functional systems 103. Functional systems 103 include electronic infrastructure 20, hospital infrastructure 30, industrial infrastructure 40, databank infrastructure 50, IT infrastructure 60, administration infrastructure 70, and utility and safety monitoring infrastructure 80. Input message system 210 can receive message alerts through various types of protocols and through various types of communication interfaces used by functional systems 103. Input message system 210 may include electronic and electric devices and modules such as computer terminals, paging terminals, computer controlled switching systems, etc. Input message system 210 accepts calls from telephone networks, emails from email systems, pages from pagers, etc. Input message system 210 may also include serial data systems, wired or IP implementations, simple stimuli sensors that detect a closed door or a pressed button, etc. Input interfaces such as TAP and SNPP input interfaces are built into input message system 210, and hence into XGate system 90A. Input message system 210 sends message alerts information to event handler system 220.

Event handler system 220 receives message alerts information from IT infrastructure 60 as well, via the UNITE modules 62. Event handler system 220 may also receive information from other software applications connected to XGate system 90A, and from other UNITE modules that may be included in hospital environment 100. Event handler system 220 may communicate with some interfaces of hospital environment 100 using the UNITE protocol. Other communication protocols for event handler system 220 can also be used.

Event handler system 220 includes software that can recognize event elements included in a message alert received from input message system 210 or from UNITE modules 62, for a multitude of message alert formats and protocols used to send message alerts. Event elements are strings of data or pieces of information from message alerts. The event elements found in a message alert contain information about the event that generated the message alert. Examples of event elements are alarm type, alarm type description, room, bed, etc. Hence, by recognizing that event elements "room" and "bed" appear in a message alert, event handler system 220 can determine that the message alert is coming from a patient's bed. Moreover, event handler system 220 can then deduce that strings of data found after each event element contain location information such as room number and bed number of the patient. Event handler system 220 extracts event elements and other elemental information from message alerts, and sends the extracted information to assignment handler system 230. Assignment handler system 230 receives extracted event elements and elemental information from message alerts from an external event handler 120 as well.

Assignment handler system 230 then performs deductions and inferences to determine the significance of the message alert, i.e. what has happened, and the identities of the people assigned to address the event described by the message alert. Assignment handler system 230 determines what underlying event caused the message alert and the personnel/teams/systems to be assigned to address the underlying event. Assignment handler system 230 then sends assignment and event information to action handler system 240 and/or external action handler 130.

External event handler 120 and external action handler 130 belong to other XGate systems 123 that may be included in hospital environment 100. For example different XGate systems may be implemented to interface with different infrastructures or systems of hospital environment 100. Hence, one XGate system may interface with nurse call systems 22, another XGate system may interface with radiology systems, yet another XGate system may interface with laboratory information systems 26, etc. Some XGate systems can be used purely for interfacing with hospital infrastructures and systems, while assignment handling can be done in a central XGate system. If XGate 90A is a central XGate system, it receives data from external event handler 120 and sends assignment data to external action handler 130 belonging to other XGate systems 123 used for interfacing with hospital infrastructures. Hence, assignment handler system 230 can connect several XGate systems into one communicating system.

When multiple XGate systems are used in hospital environment 100 and assignment handler system 230 performs assignments for multiple XGate systems, parameters are set up to differentiate between the multiple XGate systems and send the correct event and duty assignments to the appropriate XGate system. Hence, event and duty assignments for a message alert originating with radiology systems are sent to the XGate that interfaces with the radiology systems.

Action handler system 240 receives event and duty assignment information from assignment handler system 230, generates action alerts, and sends action alerts to human interface 110 and functional systems 103. Event assignment information includes information about the underlying event caused the message alert. Duty assignment information includes information about the personnel/teams/systems assigned to address the underlying event. Action handler system 240 may also send action alerts directly to external carrier gateway ECG 64 included in the UNITE modules 62 of IT infrastructure 60. ECG 64 translates the protocol of UNITE messaging blocks generated by action handler system 240 to external standard protocols understood by the system of the user, such as the TAP and the SNPP protocols.

The action alerts generated by action handler system 240 include messages and instructions to be used by personnel to address the events that initially caused the message alerts. The messages and instructions can be plain language messages, UNITE messaging blocks, etc. Action handler system 240 also generates machine action alerts to be executed by designated automated systems. Action alerts generated by action handler system 240 may trigger digital outputs, which can be used as input to automatic systems. Action alerts generated by action handler system 240 can also be SNMP (Simple Network Management Protocol) unsolicited or asynchronous traps. An unsolicited or asynchronous trap is an unsolicited SNMP message. SNMP traps enable an agent (user) to notify the management station or the network management system of significant events, by sending an unsolicited SNMP message to the network management system. Additional UNITE modules may be used to receive action alerts from action handler system 240, if action handler system 240 interfaces with functional systems 103 via other standard protocols such as OPC (Object Linking and Embedding for Process Control). OPC is an open standard designed to bridge Windows-based applications, process control hardware, and software applications. OPC protocol permits a consistent method of accessing field data from plant floor devices.

Input message system 210, event handler system 220, assignment handler system 230 and action handler system 240 are software programs/interfaces, residing on hardware such as a microprocessor, a network of microprocessors, a server, a network of servers, etc. XGate system 90A may incorporate both hardware and software. In one implementation, the XGate system is built on the Linux operating system and includes software packages/applications.

Figure 3:
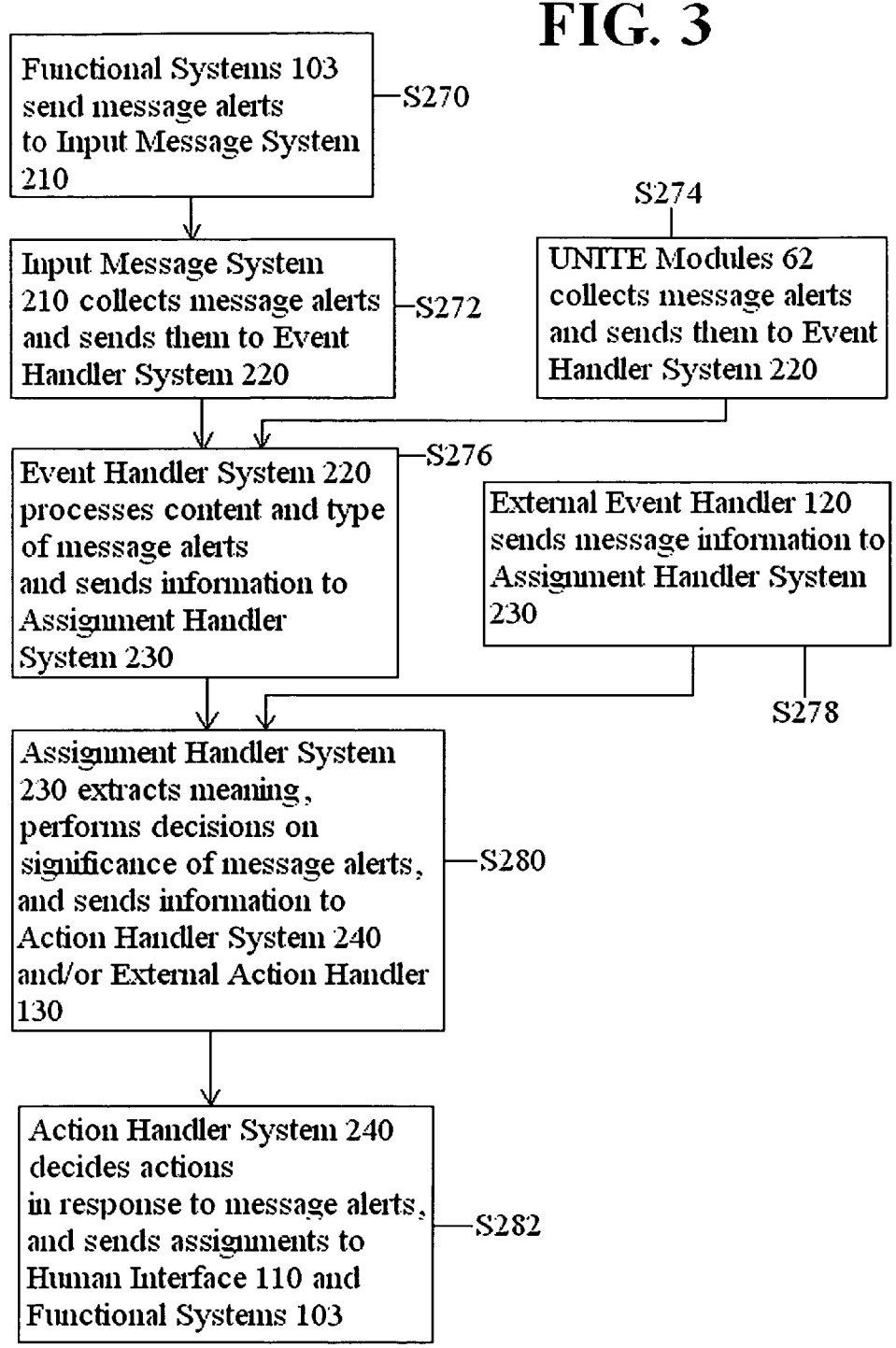
FIG. 3 is a flow diagram illustrating operations performed by an automated medical staff assignment system to perform automatic assignments and generate actions in a hospital environment according to an embodiment of the present invention.

FIG. 3 is a flow diagram illustrating operations performed by an automated medical staff assignment (XGate) system 90A to perform automatic assignments and generate actions in a hospital environment 100 according to an embodiment of the present invention. Functional systems 103 send message alerts to input message system 210 (S270). If NetPage is used, human interface 110 may also send message alerts to input message system 210. Input message system 210 receives the message alerts and sends them to event handler system 220 (S272). UNITE modules 62 also collect message alerts and send the alerts to event handler system 220 (S274). Event handler system 220 processes the content and type of received message alerts to extract elemental information from the message alerts (S276). Event handler system 220 then sends the extracted message alerts information to assignment handler system 230 (S276). Assignment handler system 230 receives message alerts information from external event handler 120 as well (S278). Assignment handler system 230 assigns meaning to the message-alert information received, and performs assignments of personnel and/or systems to address the events that caused the message alerts (S280). Assignment handler system 230 then sends the assignments and message significance information to action handler system 240 and/or external action handler 130 (S280). Action handler system 240 decides actions to be performed in response to message alerts, and sends action requests to assigned personnel and/or systems in human interface 110 and functional systems 103 (S282).

Figure 4:
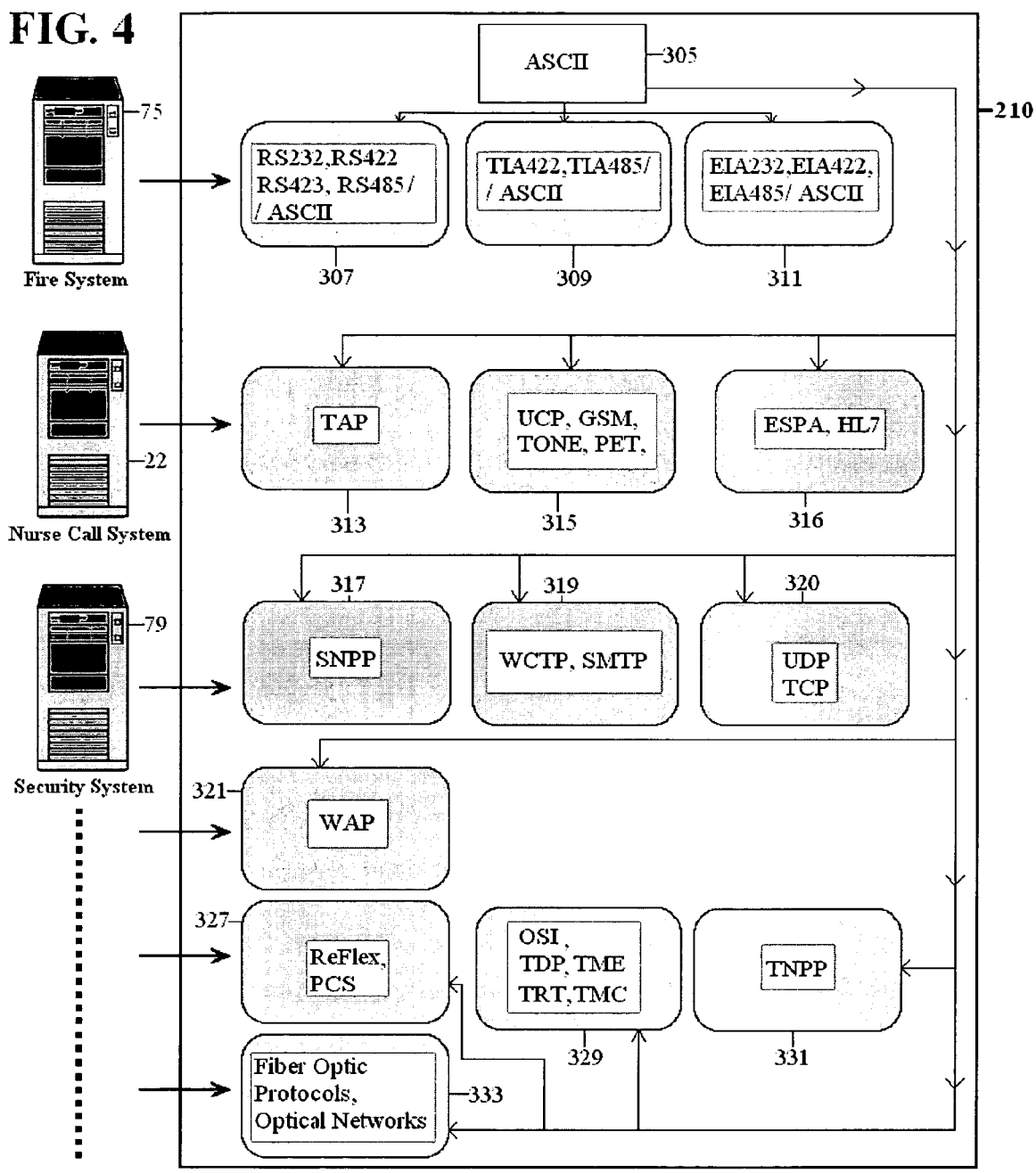
FIG. 4 is a block diagram of an input message system included in an automated medical staff assignment system according to an embodiment of the present invention illustrated in FIG. 2.

FIG. 4 is a block diagram of an input message system 210 included in an automated medical staff assignment (XGate) system 90A according to an embodiment of the present invention illustrated in FIG. 2. A few systems belonging to functional systems 103 are shown in FIG. 4 to facilitate the understanding of the block diagram. A fire system 75 included in utility and safety monitoring infrastructure 80, a nurse call system 22 included hospital infrastructure 30, and a security system 79 included in utility and safety monitoring infrastructure 80 send message alerts to input message system 210.

Input message system 210 includes physical network medium interfaces 307, 309 and 311 that receive message alerts from fire system 75. Physical network medium interface 307 receives message alerts through RS232, RS422, RS423 and RS485 communication data interfaces. The RS232, RS422, RS423 and RS485 specifications define the physical (hardware) implementation and the electrical implementation of the bus, the network cabling, the connector type, the pin-out, the physical data rates, the maximum transmission distances, and the data transmission encoding of communication data interface 307. The data may be presented in ASCII code, however, other standards and formats for presentation of data may be possible. ASCII Input Interface 305 presents data in ASCII code. Physical network medium interface 309 receives message alerts through TIA422 and TIA4858 communication data interfaces. Physical network medium interface 311 receives message alerts through EIA232, EIA422 and EIA485 communication data interfaces. EIA and TIA data interfaces are more recent versions of the RS data interface, defined by the Electronic Industries Alliance (EIA) and the Telecommunications Industry Association (TIA).

Input message system 210 also includes interfaces 313, 315 and 316 that receive message alerts from nurse call system 22. Interface 313 receives message alerts through the TAP protocol, which is a telelocator alphanumeric protocol that allows for messages to be sent through modem to a paging terminal in a format that the paging terminal understands. Interface 315 receives message alerts through the UCP, TONE, PET or GSM protocols. UCP is a protocol similar to the TAP protocol. PET is a paging protocol that preceded the TAP protocol. TONE is a protocol used with modems. GSM, which stands for Global System for Mobile communication, is a European digital standard for mobile or cellular telephony. Interface 316 receives message alerts through the ESPA and HL7 protocols. ESPA is a serial protocol intended for the interconnection of paging equipment with telephone exchanges systems or computer systems. HL7 (Health Level Seven) is a standard for information exchange between medical applications. HL7 is the 7th OSI layer protocol, used for the health environment system. HL7 is a protocol for inter-system data exchange of message applications. For example, an application that encounters a real world event, such as an emergency patient being brought in, sends a message through the HL7 protocol to other applications that need to be aware of the real world event.

Input message system 210 also includes interfaces 317, 319 and 320 to receive message alerts from security system 79. Interface 317 receives message alerts via the Internet using the SNPP protocol, which is a network paging protocol that allows for messages to be sent through the Internet to pagers and cell phones. Interface 319 receives message alerts via the WCTP and SMTP protocols. WCTP is a wireless communication transfer protocol allows for messages to be sent through the Internet to pagers and cell phones. SMTP, which stands for Simple Mail Transfer Protocol, is a simple, text-based protocol used for e-mail transmission, where one or more recipients of a message are specified and then the message text is transferred. Interface 320 receives message alerts via the UDP and TCP protocols. The UDP protocol, which stands for User Datagram Protocol, is a transport layer protocol used with the Internet Protocol, and provides datagram service to an Internet Protocol host. The TCP protocol, which stands for Transmission Control Protocol, is one of the core protocols of the Internet protocol suite. The TCP protocol is the intermediate layer between the Internet Protocol (IP) below it, and software applications above it. TCP supports Internet application protocols, as well as other applications such as the World Wide Web, email and Secure Shell.

Input message system 210 also includes interfaces 321, 323, 325, 327, 329, 331 and 333 for receiving message alerts from other systems included in functional systems 103. Interface 321 receives message alerts from functional systems 103 through the WAP protocol, which stands for Wireless Application Protocol and is an open, global specification system that empowers mobile users with wireless devices to easily access and interact with information and services instantly.

Interface 327 receives message alerts from functional systems 103 through the ReFlex protocol and PCS services. The ReFlex is a new set of two-way paging protocols developed by Motorola for enhanced paging services, supporting outbound transfer rates of up to 6,400 bits per second in a 25 kHz channel and 12,800 bits per second in a 50 kHz channel. PCS, which stands for Personal Communications Services, are a new generation of digital, two-way, low powered wireless services in the 800 to 900 MHz bands that support a wide range of services including confirmed delivery of message, full two-way data transfer, voice messaging and connectivity via the Internet.

Interface 329 receives message alerts from functional systems 103 through the OSI, TDP, TME, TRT and TMC protocols. OSI stands for Open Systems Interconnect, and is an industry wide protocol standard consisting of seven well defined layers that define communication protocols for intercomputer networking. TDP, which stand for Telocator Data Protocol, is modeled after the OSI standard. TDP is a suite of protocols used for sending messages from a computer, through a paging system, to a mobile receiving computer. TME, TRT, and TMC are part of the TDP suite. The TDP suite protocols define the flow of messages from input devices through several processing steps until the entire message is received by an RF linked computer. Interface 331 receives message alerts from functional systems 103 through the TNPP protocol, which is a protocol used for moving pages from one paging system to another over standard lines. Interface 333 receives message alerts from functional systems 103 through fiber optic protocols and optical networks.

The list of interfaces described above to be part of input message system 210 is not exhaustive. Additional communication interfaces may be included in input system 210 depending on the protocols/methods of message transmission used by systems and infrastructures of hospital environment 100.

Figure 5:
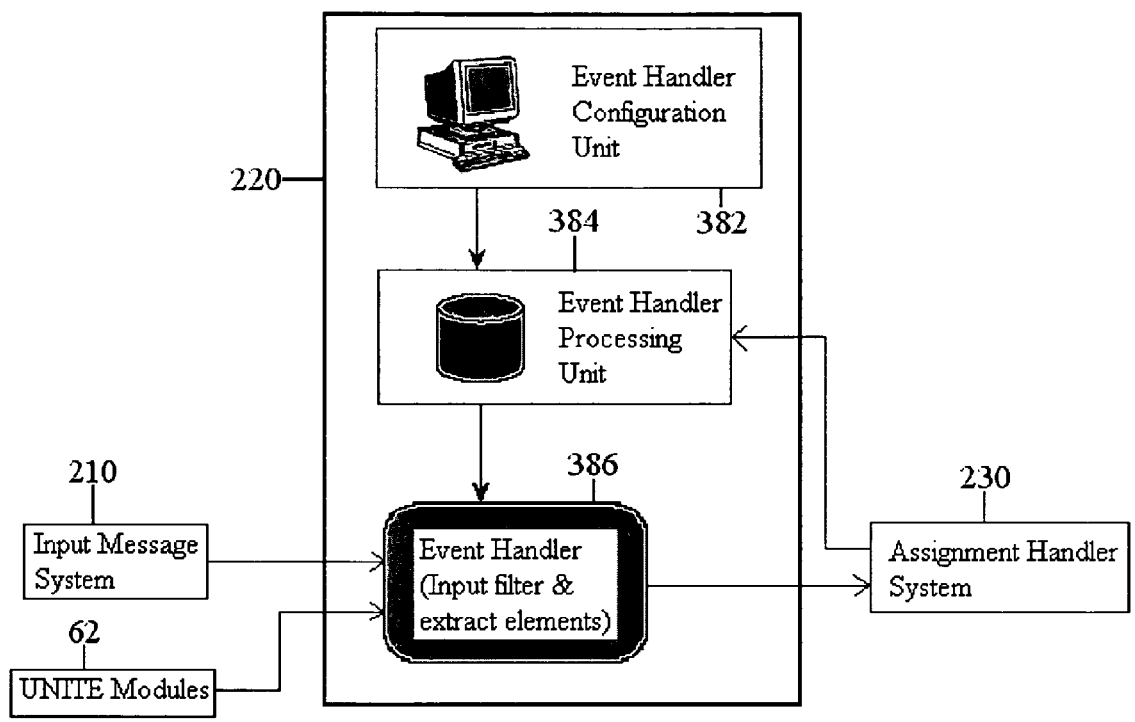
FIG. 5 is a block diagram of an event handler system included in an automated medical staff assignment system according to an embodiment of the present invention illustrated in FIG. 2.

FIG. 5 is a block diagram of an event handler system 220 included in an automated medical staff assignment (XGate) system 90A according to an embodiment of the present invention illustrated in FIG. 2. Event handler system 220 includes the following components: event handler configuration unit 382; event handler processing unit 384; and event handler 386. The event handler configuration unit 382 provides a Graphical User Interface (GUI) for setting the configuration of event handler system 220. The configuration of event handler system 220 may be set during initial setup of XGate system 90A. Event handler processing unit 384 includes a database of available event elements. Event handler 386 implements the run-time component of event handler system 220. The event handler system 220 is set up to receive message alerts from external systems and automatically extract information included in the message alerts. Event handler system 220 provides an automated way to extract message information from, for example, strings of data.

Event handler configuration unit 382 contains configuration information and filters for reading message alerts sent through various protocols. Event handler configuration unit 382 also contains configuration information needed to set up actions and events, access rights, escalation chains, success/failure conditions for event response actions, etc. Event handler configuration unit 382 can also be used to administrate the XGate system 90A and add languages and translations to XGate system 90A. The configuration information of event handler configuration unit 382 is typically set up during a first time setup, and before actions and events are implemented in XGate system 90A. Event handler configuration unit 382 is a web based GUI residing on the XGate system 90A. Event handler configuration unit 382 sends the configuration information and filters to event handler processing unit 384. Event handler processing unit 384 then sends the configuration information and filters to event handler 386. Event handler processing unit 384 receives additional information useful in reading message alerts, such as event elements, from assignment handler system 230 and sends the additional information to event handler 386.

Event handler 386 receives message alerts from input message system 210 and UNITE modules 62. Upon receiving a message alert, event handler 386 retrieves configurations and filters from the database located in event handler processing unit 384, reads message alerts using the right configuration and filters, and sends the extracted message information to assignment handler system 230.

Event handler configuration unit 382, event handler processing unit 384, and event handler 386 are software applications/packages, and reside on the hardware that supports XGate.

Figure 6:
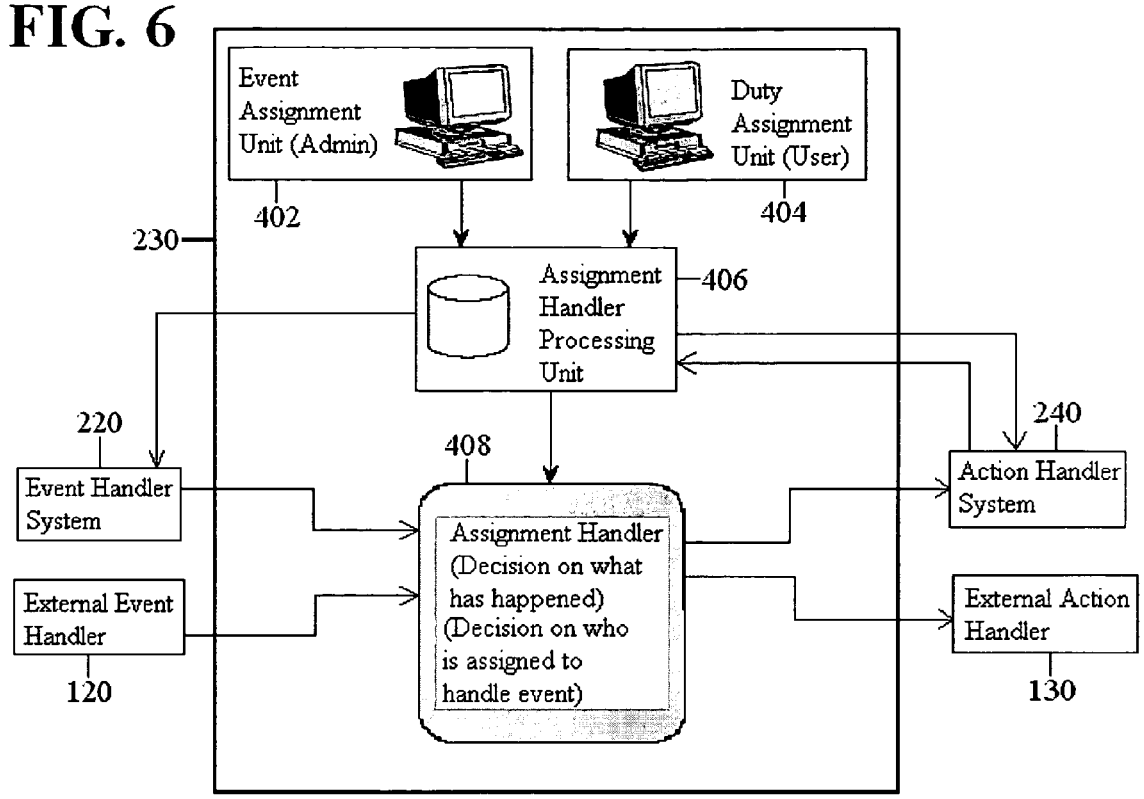
FIG. 6 is a block diagram of an assignment handler system included in an automated medical staff assignment system according to an embodiment of the present invention illustrated in FIG. 2.

FIG. 6 is a block diagram of an assignment handler system 230 included in an automated medical staff assignment (XGate) system 90A according to an embodiment of the present invention illustrated in FIG. 2. Assignment handler system 230 includes the following components: event assignment unit (admin) 402; duty assignment unit (user) 404; assignment handler processing unit 406; and assignment handler 408.

Event assignment unit (admin) 402 and duty assignment unit (user) 404 contain events, actions associated with events, type of information needed for actions, success/failure criteria for actions, locations layouts, user data, user teams data, etc. Event assignment unit (admin) 402 and duty assignment unit (user) 404 have GUI functionality. Information about actions and events can be entered by administration in event assignment unit (admin) 402 using the graphical user interface. The administration personnel also administrate duty assignments through event assignment unit (admin) 402. Event elements, which contain information about an event, are defined in event assignment unit (admin) 402. Examples of event elements are alarm type such as patient alarm type, alarm type description, room number, bed number, etc. When new events are entered in event assignment unit (admin) 402, a synchronization function may be executed to update the databases of XGate 90A with the new events and event elements and indicate that new event elements for the new events are to be entered in event assignment unit (admin) 402.

Assignments of events to users are done by users in the duty assignment unit (user) 404 using the graphical user interface. Users can select from a list of persons, teams, or systems set up by administration personnel, the person/team/system to address a message alert. Hence, event assignment unit (admin) 402 and duty assignment unit (user) 404 are typically used by different users (administration personnel vs. users). Administration personnel define events and assignment lists in event assignment unit (admin) 402, while users set up duty assignments on a daily basis using the duty assignment unit (user) 404.

Event assignment unit (admin) 402 and duty assignment unit (user) 404 send the admin-defined and user-defined event information to assignment handler processing unit 406. Assignment handler processing unit 406 includes databases of available event elements and available events. Assignment handler processing unit 406 may receive additional information useful in interpreting events from action handler system 240. Assignment handler processing unit 406 then sends the admin-defined and user-defined event information to assignment handler 408. Assignment handler processing unit 406 also sends event information to action handler system 240 and event handler system 220.

Assignment handler 408 receives extracted message alert information from event handler system 220 and/or external event handler 120. Using admin-defined and user-defined event information, assignment handler 408 decides what events generated the message alerts. Assignment handler 408 also assigns a person, or multiple persons/teams/systems to respond to the message alerts. Assignment handler system 230 uses multiple parameters in order to determine assignments, and exhibits high flexibility in handling incoming data by being able to use any part of received event data strings. Assignment handler 408 then sends the event and assignment information to action handler 240 and/or external action handler 130. Information is sent to external action handler 130 when, for example, external action handler 130, which is part of another XGate system, is at a different geographic location than XGate system 90A.

Event assignment unit (admin) 402, duty assignment unit (user) 404, assignment handler processing unit (406), and assignment handler 408 are software packages/applications that reside on the hardware that supports XGate.

Assignment handler system 230 also includes login functionality that prohibits unauthorized personal from accessing or tampering with the setup of XGate system 90A. Administration personnel and system administration personnel use logins and passwords to access the event assignment unit (admin) 402 and the duty assignment unit (user) 404. Administration personnel assign logins and passwords for users to access the duty assignment unit (user) 404. Users then use logins and passwords to access the duty assignment unit (user) 404.

Figure 7:
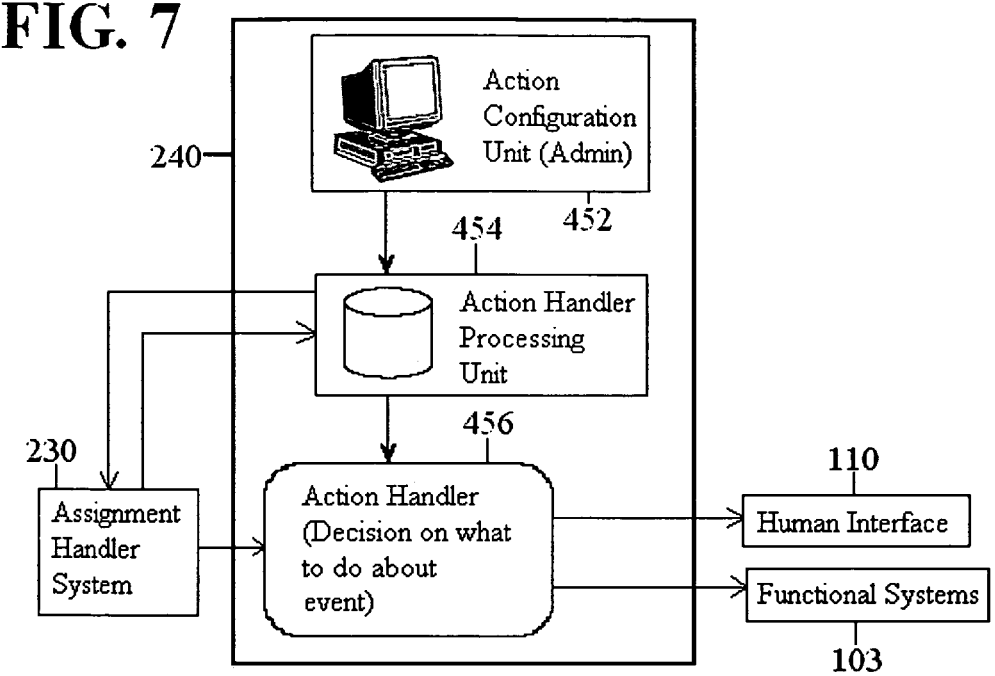
FIG. 7 is a block diagram of an action handler system included in an automated medical staff assignment system according to an embodiment of the present invention illustrated in FIG. 2.

FIG. 7 is a block diagram of an action handler system 240 included in an automated medical staff assignment (XGate) system 90A according to an embodiment of the present invention illustrated in FIG. 2. Action handler system 240 includes the following components: action configuration unit (admin) 452; action handler processing unit 454; and action handler 456.

Action configuration unit (admin) 452 contains admin-defined action configurations for events that generate message alerts. Such action configurations include what type of message and content to transmit for a given event, success and failure conditions for actions, etc. Example of actions are: requests to send a message to a specific destination, with confirmation request that action will be performed; requests to send a message to a specific destination with different interactive response options included; requests to set or reset an output such as requests to remotely turn on or off an alarm; requests to erase a previously sent message; etc. Action messages may include options such as: adding a message response; request for acknowledgement accept when the receiver has read the message; request for acknowledgement with accept and reject options, where the receiver has the option to reject the message; etc. Action requests can be addressed to predefined users, to predefined call IDs, and to users identified in the duty assignment unit (user) 404.

When new events are entered in event assignment unit (admin) 402, a synchronization function can be executed to update the event and event elements databases with new events and new event elements, and indicate that new actions for the new events are to be input in action configuration unit (admin) 452.

Action configuration unit (admin) 452 saves the admin-defined actions and action configurations and sends them to action handler processing unit 454. Action handler processing unit 454 is a database that is used in run-time by action handler 456. Action handler processing unit 454 includes databases of available events and available event elements. After action configuration unit (admin) 452 sends admin-defined action information to action handler processing unit 454, action handler processing unit 454 sends the admin-defined action information to action handler 456. Action handler processing unit 454 receives additional information including event elements from assignment handler system 230, and sends the additional information to action handler 456. Action handler processing unit 454 communicates back with assignment handler system 230 by sending relevant event information obtained from action configuration unit (admin) 452. Such relevant event information may include available events information.

Action handler 456 receives event information and assignment information from assignment handler system 230. The event information reaching action handler 456 includes data received in the message alert describing the underlying event. Depending on how XGate system 90A is set up, the event information reaching action handler 456 includes original data received in the message alert, as well as data from the message alert that was translated by XGate system 90A.

Using admin-defined action information received from action handler processing unit 454, action handler 456 generates and sends action requests to human interface 110 and functional systems 103. Action chains can be set up by XGate system 90A with alternative actions for one event. The alternative actions depend on multiple factors such as availability of personnel. Action handler 456 can also handle two-way messages, thus enabling the user to acknowledge or reject the action request message.

Action configuration unit (admin) 452, action handler processing unit 454, and action handler 456 are software packages/applications that reside on the hardware that supports XGate. In one implementation, the operating system (Linux) is common for the software applications on XGate.

Figure 8:
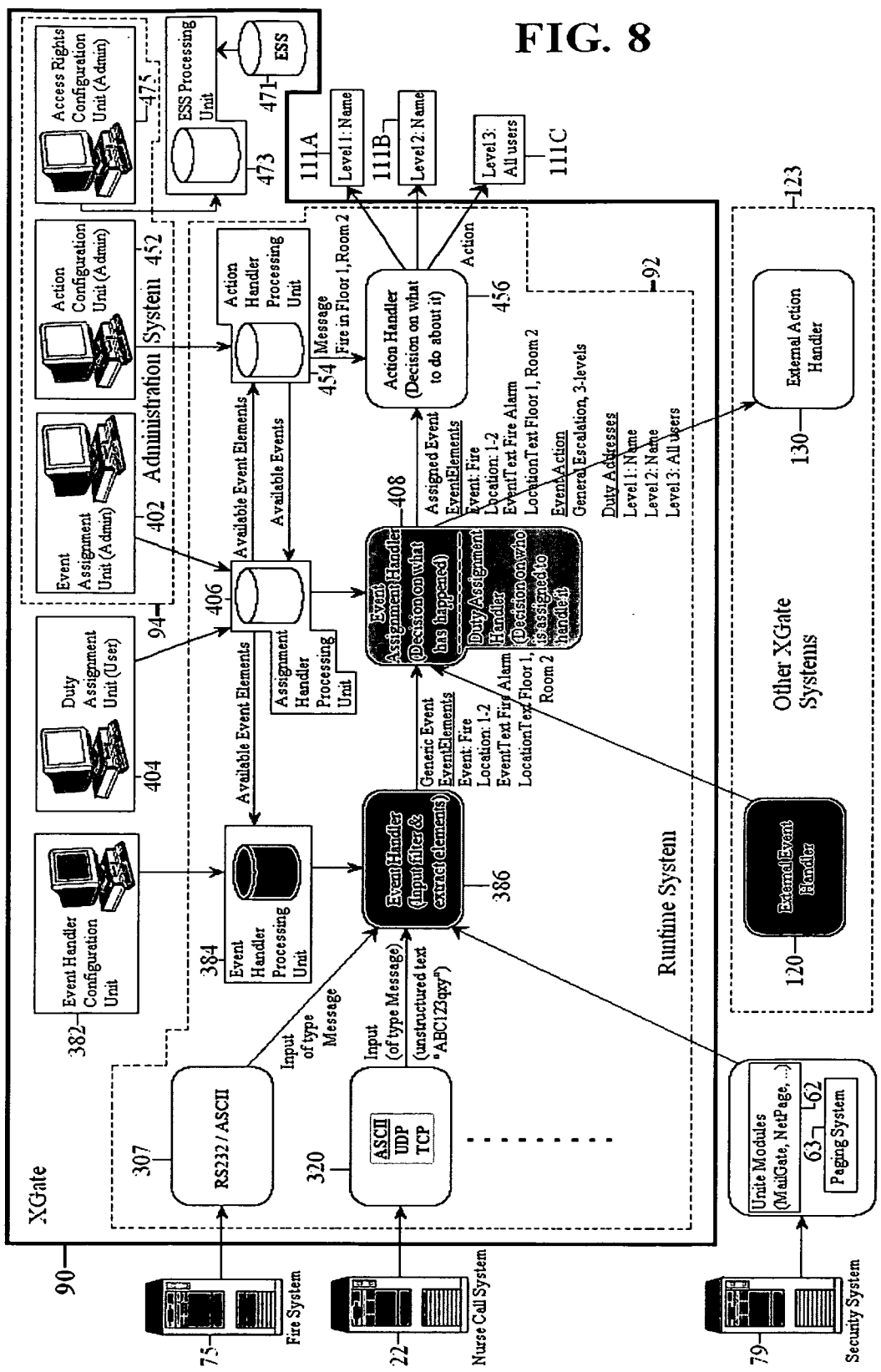
FIG. 8 is a block diagram of an automated medical staff assignment system according to an embodiment of the present invention.

FIG. 8 is a block diagram of an automated medical staff assignment (XGate) system 90 according to an embodiment of the present invention. FIG. 8 shows a detailed diagram of XGate system 90 using block information presented in FIGS. 4, 5, 6 and 7. XGate system 90 includes the following components: input message system 210 of which data interfaces 307 and 320 for RS232/ASCII interfacing and ASCII/UDP and TCP interfacing are shown; event handler configuration unit 382; event handler processing unit 384; event handler 386; duty assignment unit (user) 404; event assignment unit (admin) 402; assignment handler processing unit 406; assignment handler 408; action configuration unit (admin) 452; action handler processing unit 454; action handler 456; access rights configuration unit (admin) 475; Enhanced System Services (ESS) processing unit 473; and Enhanced System Services (ESS) unit 471. The main data transport path in XGate 90 is from the data interfaces 307 and 320 of input message system 210, to event handler 386, assignment handler 408, action handler 456, and then out to functional systems 103 and optionally to human interface 110.

Access rights configuration unit (admin) 475 includes configurations for storing login and password information that defines access rights for administration personnel, and sets access rights of users and user teams. Access rights configuration unit (admin) 475 includes a graphical user interface (GUI) for access rights configuration. ESS unit 471 is a UNITE module containing user info, such as teams, team members, user work-shift data, etc. ESS processing unit 473 communicates access rights and user info to duty assignment unit (user) 404, event assignment unit (admin) 402, and action configuration unit (admin) 452. Access rights in XGate system 90 for accessing the duty assignment unit (user) 404 are set by the XGate administrator.

The assignment handler 408 has been split into two sub-units. One sub-unit handles event assignments (i.e. decides what event occurred that generated the message alert). The other sub-unit handles duty assignments (i.e., decides who is assigned to handle the event).

XGate system 90 includes graphical user interfaces and runtime systems. The input message system 210 of which data interfaces 307 and 320 for are shown, event handler processing unit 384, event handler 386, assignment handler processing unit 406, assignment handler 408, action handler processing unit 454, and action handler 456 form the Runtime System 92 of XGate system 90, which is active during run-time. The event assignment unit (admin) 402, action configuration unit (admin) 452, access rights configuration unit (admin) 475, and duty assignment unit (user) 404 are GUI interfaces of XGate system 90. The graphical user interfaces of event assignment unit (admin) 402, action configuration unit (admin) 452, and access rights configuration unit (admin) 475 form the administration system 94, which is accessible to the administration personnel.

Event handler 386 receives message input information from RS232 interface 307, UDP and TCP interface 320, the other interfaces (not shown) of input message system 210, UNITE Modules 62, paging system 63, etc. Assignment handler 408 communicates with other XGate systems 123 that include external event handlers 120 and external action handlers 130. Hence, several XGate modules can work together in a system, when they are connected by the assignment handler 408 of a central XGate system.

In one implementation, the admin GUI interfaces of event assignment unit (admin) 402, action configuration unit (admin) 452, access rights configuration unit (admin) 475, and the user GUI interface of duty assignment unit (user) 404 are web-based and can be accessed once XGate system 90 is installed on the LAN of hospital environment 100. To access any of the GUI interfaces, user ID and password are required. The administrative personnel can add additional users that will have access to the duty assignment unit GUI 404. The user interfaces 404, 402, 452, 475 of XGate system 90 are used for setting up elements and properties for XGate system 90. XGate system 90 operates automatically during run-time, without intervention or monitoring from the user interfaces.

During run-time, events are automatically handled by XGate system 90, and actions for events are automatically generated according to the settings made in the user interfaces 404, 402, 452, 475. Users and administration personnel do not need to monitor events and actions over the XGate web GUIs of XGate system 90. Hence, XGate system 90 can handle message alerts, events and actions automatically. When an action message is rejected by the intended user, or the action message can not be delivered, XGate system 90 performs an automatic escalation of actions to multiple levels, in order to identify a user that will receive the action message and execute it. In one exemplary implementation, XGate can perform escalation of actions up to 5 levels.

XGate system 90 includes both hardware and software. In one implementation, the XGate software consists of Linux Operating System and a number of additional software applications.

For exemplification purposes, the path through XGate system 90 of a fire message alert is shown. The fire message alert is received from the fire system 75 through the RS232/ASCII interface 307. Input message system 210 classifies the fire message alert as an input of type message containing numeric and alphanumeric characters in unstructured text such as "ABC123qxy". Event handler 386 receives the input of type message and decides on the configuration compatible with the protocol type of interface 307, from where the initial message alert was received. Using the correct configuration, event handler 386 is able to read and extract event elements from the input of type message. The event elements are output in categories such as "Event", "Location", "EventText" and "LocationText". The event elements for the fire alarm are:
EventElements:
Event: Fire
Location 1-2
EventText Fire Alarm
LocationText Floor1, Room2.

Event handler processing unit 384 includes a database. Data, including event elements, is transferred from event handler processing unit 384 to event handler 386. On request, data can also be transferred from event handler 386 to event handler processing unit 384. Similarly, assignment handler processing unit 406 includes a database, and the data is transferred from assignment handler processing unit 406 to assignment handler 408. On request, data can also be transferred from assignment handler 408 to assignment handler processing unit 406. In a similar manner, action handler processing unit 454 includes a database, so the data is transferred from action handler processing unit 454 to action handler 456. On request, data can also be transferred from action handler 456 to action handler processing unit 454.

At this point the event is classified as a Generic Event, as a meaning has not been yet assigned to the event elements. The Generic Event is sent to assignment handler 408. Upon reading the Event Element EventText "Fire Alarm" and searching through a database of correspondence between events meaning and event names, assignment handler 408 decides that a fire has occurred. The database of correspondence between events meaning and event names is located in assignment handler processing unit 406. Assignment handler 408 then retrieves the appropriate duty assignments and escalation paths for a fire event from event assignment unit (admin) 402 and duty assignment unit (user) 404. Assignment handler 408 processes the appropriate assignments and escalation paths and outputs an Assigned Event which includes "Event Action" and "Duty Addresses" categories. The Assigned Event output for the fire alarm is of the following form:
EventElements
Event: Fire
Location 1-2
EventText Fire Alarm
LocationText Floor1, Room2.
EventAction
General escalation, 3-levels
DutyAddresses
Level 1: Name
Level 2: Name
Level 3: All users The assigned event is sent to action handler 456. The event elements "Event: Fire", "Location 1-2", "EventText Fire Alarm", and "LocationText Floor1, Room2" of the Assigned Event are also sent to action handler processing unit 454 via assignment handler processing unit 406. While assignment handler processing unit 406 and action handler processing unit 454 contain data on how to transform an input message into an assigned event, event handler 386 and assignment handler 408 hold information during run-time about what event occurred, and execute the logic for converting an input message into an action.

Using the received event elements, action handler processing unit 454 composes a message in plain English describing the event: "Fire in Floor 1, Room 2". Action handler processing unit 454 sends the composed message to action handler 456. Action handler 456 accesses the assignment information received from assignment handler 408, and sends the composed message together with action requests to the assigned personnel 111A, 111B and 111C listed under the field Duty-Addresses in the information received from assignment handler 408.

Action handler 456 secures that the action messages are delivered to the intended receivers. Action handler 456 detects paging acknowledge as well as a number of other possible replies. Confirmatory replies for outgoing actions may be received by action handler 456 from users 111A, 111B or 111C. XGate system 90 can act differently after receiving replies, depending on the reply received and depending on other relevant information such as time-of-day. XGate system 90 is also capable of handling more advanced two-way communication using paging or telephone equipment. XGate system 90 thus makes it possible to create complex action chains, using web based user interfaces to set up such advanced action chains. The content of the action message can also be altered along the chain, e.g. to include information on the original destination.

Figure 9:
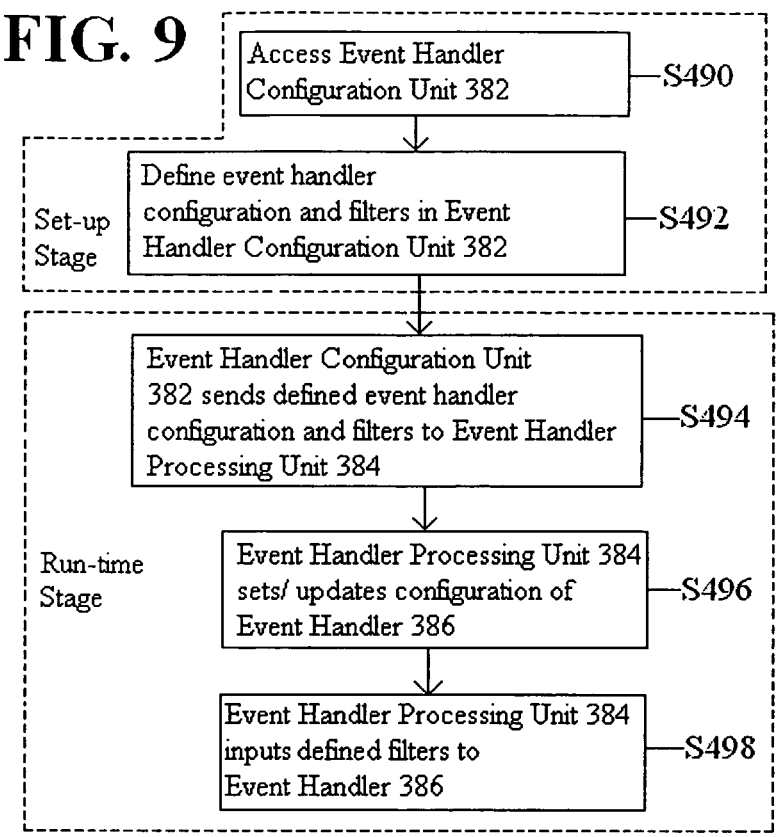
FIG. 9 is a flow diagram illustrating operations performed by an event handler system included in an automated medical staff assignment system according to an embodiment of the present invention illustrated in FIG. 8.

FIG. 9 is a flow diagram illustrating operations performed by an event handler system 220 included in an automated medical staff assignment (XGate) system 90 according to an embodiment of the present invention illustrated in FIG. 8. Event handler configuration unit 382 is accessed during a set-up session (S490) and event handler configurations and filters are defined in event handler configuration unit 382 (S492). Steps S490 and S492 are performed during a set-up stage of XGate system 90.

Event handler configuration unit 382 then sends event handler configurations and filters to event handler processing unit 384 (S494). Event handler processing unit 384 sets/updates configurations of event handler 386 with configurations (S496). Event handler processing unit 384 also inputs/updates filters in event handler 386 (S498). Steps S494, S496 and S498 are performed during the operation stage (i.e. runtime stage) of XGate system 90.

Figure 10A:
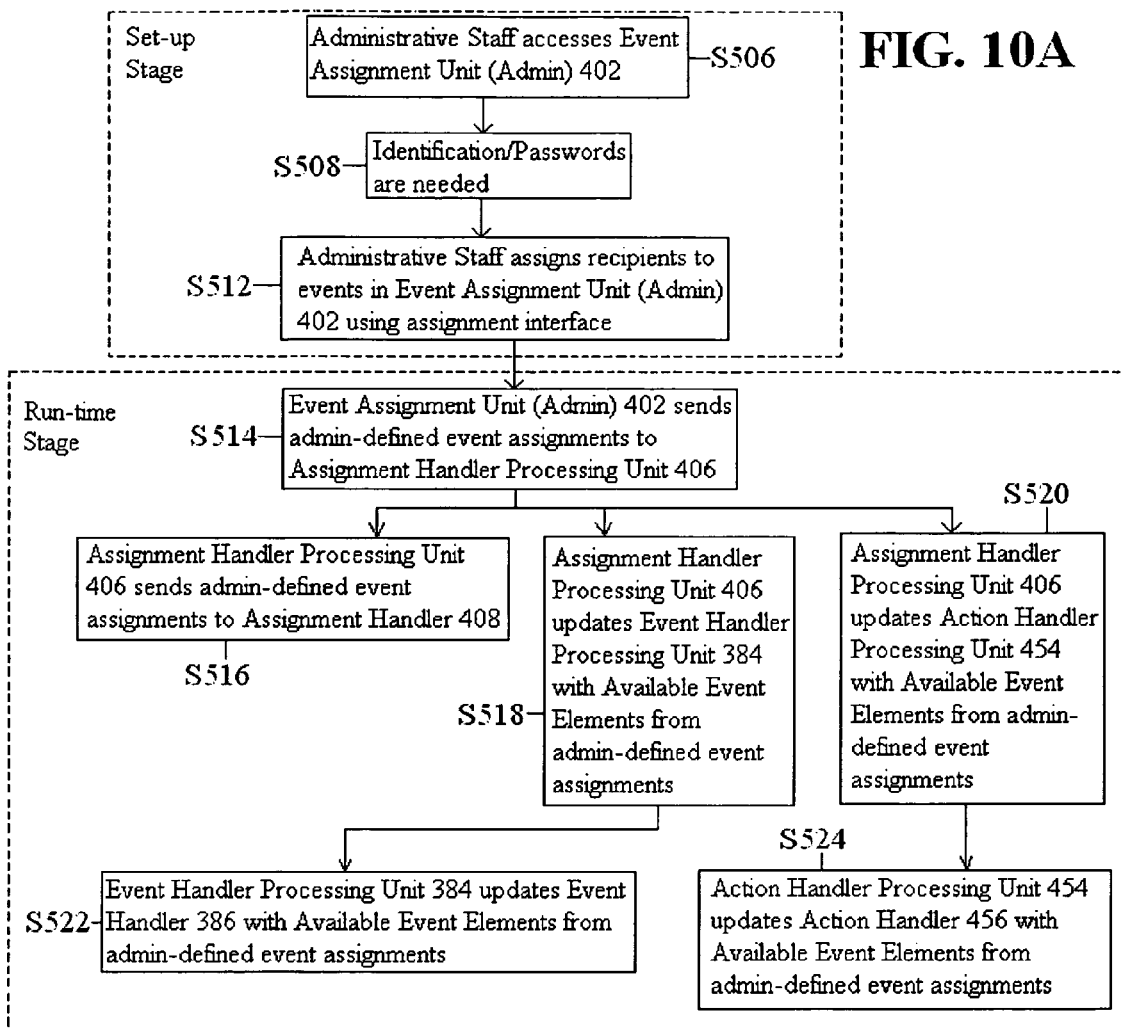
FIG. 10A is a flow diagram illustrating operations performed by an assignment handler system included in an automated medical staff assignment system and using administration-defined event and assignment information, according to an embodiment of the present invention illustrated in FIG. 8.

FIG. 10A is a flow diagram illustrating operations performed by an assignment handler system 230 included in an automated medical staff assignment (XGate) system 90 and using administration-defined event and assignment information according to an embodiment of the present invention illustrated in FIG. 8. During a set-up stage of XGate system 90, administrative staff accesses the event assignment unit (admin) 402 (S506). Identification/passwords are needed to access the event assignment unit (admin) 402 (S508). After accessing the event assignment unit (admin) 402, administrative staff assigns recipients to events in event assignment unit (admin) 402 using an assignment interface (S512).

During the run-time stage of XGate system 90, event assignment unit (admin) 402 sends admin-defined event assignments to assignment handler processing unit 406 (S514). Assignment handler processing unit 406 sends admin-defined event assignments to assignment handler 408 (S516). Assignment handler processing unit 406 also updates event handler processing unit 384 with available event elements present in admin-defined event assignments (S518). Event handler processing unit 384 then updates event handler 386 with available event elements from admin-defined event assignments (S522). Finally, assignment handler processing unit 406 updates action handler processing unit 454 with available event elements present in admin-defined event assignments (S520), and action handler processing unit 454 in turn updates action handler 456 with available event elements from admin-defined event assignments (S524).

Figure 10B:
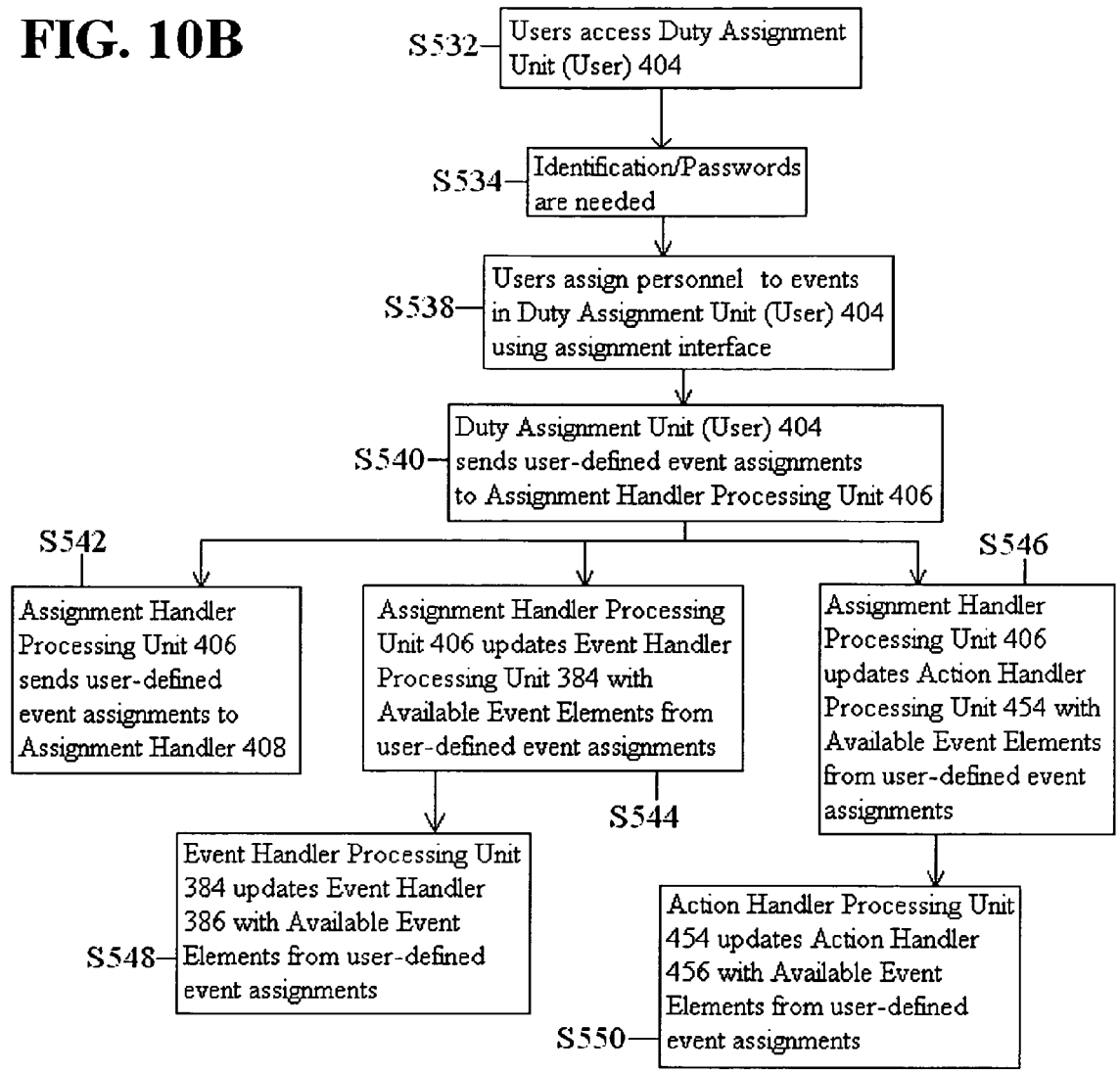
FIG. 10B is a flow diagram illustrating operations performed by an assignment handler system included in an automated medical staff assignment system and using user-defined assignment information, according to an embodiment of the present invention illustrated in FIG. 8.

FIG. 10B is a flow diagram illustrating operations performed by an assignment handler system 230 included in an automated medical staff assignment (XGate) system 90 and using user-defined assignment information according to an embodiment of the present invention illustrated in FIG. 8. FIG. 10B is similar to FIG. 10A, however FIG. 10B describes operations originating in duty assignment unit (user) 404.

Users access the duty assignment unit (user) 404 (S532). Identification/passwords are needed to access the duty assignment unit (user) 404 (S534). Users assign personnel to events in duty assignment unit (user) 404 using an assignment interface (S538). The users may be persons that are in charge only of making assignments, or they may be personnel listed in duty assignment unit (user) 404. In a hospital environment, one person (user) typically is in charge of making assignments for all personnel in the hospital ward. Duty assignment unit (user) 404 then sends user-defined event assignments to assignment handler processing unit 406 (S540). Assignment handler processing unit 406 sends user-defined event assignments to assignment handler 408 (S542). Assignment handler processing unit 406 also updates event handler processing unit 384 with available event elements from user-defined event assignments (S544). Event handler processing unit 384 then updates event handler 386 with available event elements from user-defined event assignments (S548). Finally, assignment handler processing unit 406 updates action handler processing unit 454 with available event elements from user-defined event assignments (S546), and in turn action handler processing unit 454 updates action handler 456 with available event elements from user-defined event assignments (S550).

The steps in FIG. 10B may all be performed during the run-time stage of XGate system 90. The steps S532, S534 and S538 may also be performed during a set-up stage of XGate system 90.

Figure 11:
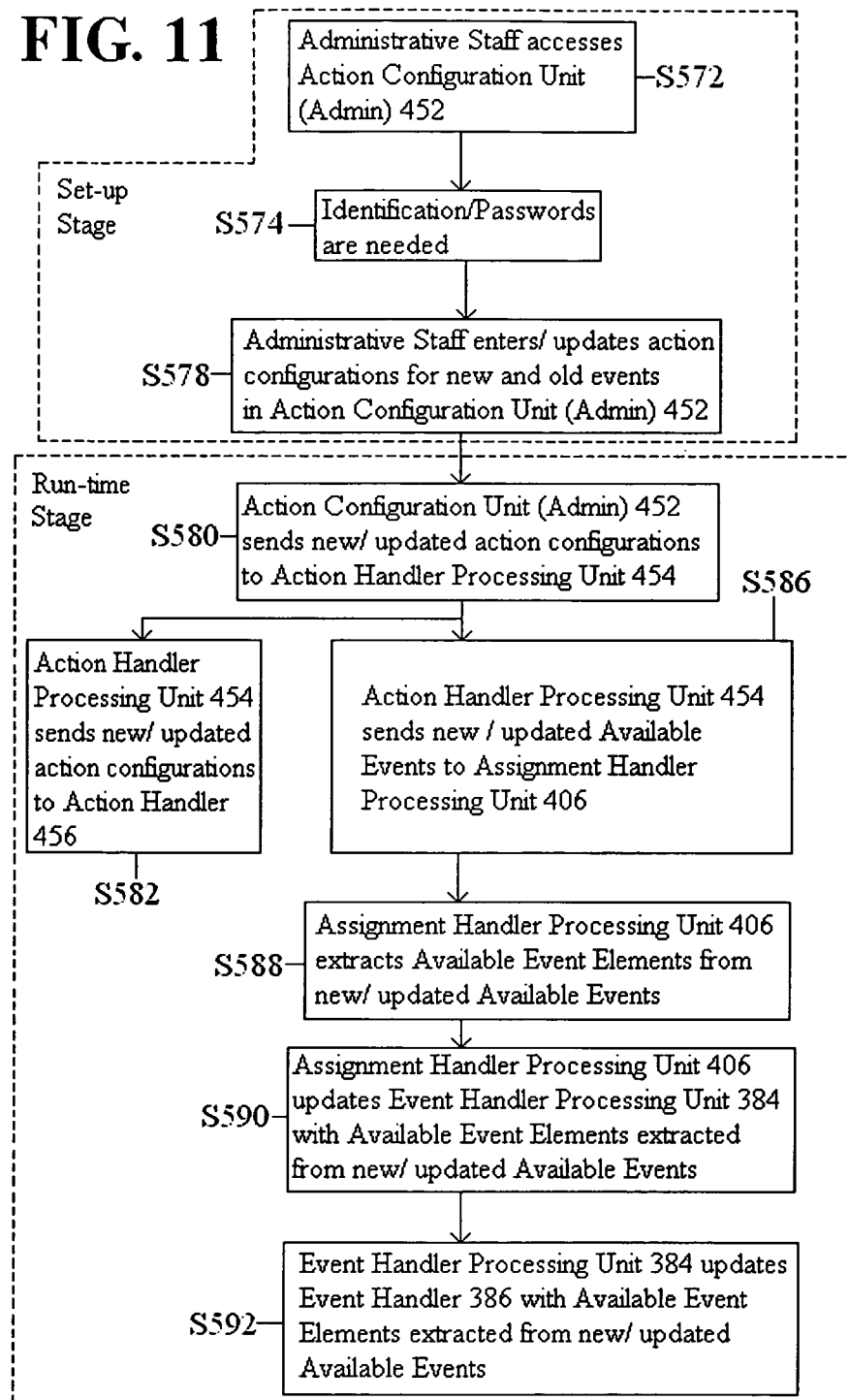
FIG. 11 is a flow diagram illustrating operations performed by an action handler system included in an automated medical staff assignment system according to an embodiment of the present invention illustrated in FIG. 8.

FIG. 11 is a flow diagram illustrating operations performed by an action handler system 240 included in an automated medical staff assignment (XGate) system 90 according to an embodiment of the present invention illustrated in FIG. 8. Administrative staff accesses action configuration unit (admin) 452 (S572). Identification/passwords are needed to access the action configuration unit (admin) 452 (S574). After accessing action configuration unit (admin) 452, administrative staff enters/updates action configurations for new and old events in action configuration unit (admin) 452 (S578). The steps S572, S574 and S578 are performed during a set-up stage of XGate system 90.

Action configuration unit (admin) 452 then sends new/updated action configurations to action handler processing unit 454 (S580). Action handler processing unit 454 then sends new/updated action configurations to action handler 456 (S582). Action handler processing unit 454 also sends new/updated available events included in new/updated action configurations to assignment handler processing unit 406 (S586). Assignment handler processing unit 406 extracts available event elements from new/updated available events received (S588), and updates event handler processing unit 384 with the available event elements extracted (S590). Event handler processing unit 384 in turn updates event handler 386 with available event elements received from event handler processing unit 384 (S592). Steps S580, S582, S586, S588, S590 and S592 are performed during the run-time stage of XGate system 90.

Figure 12:
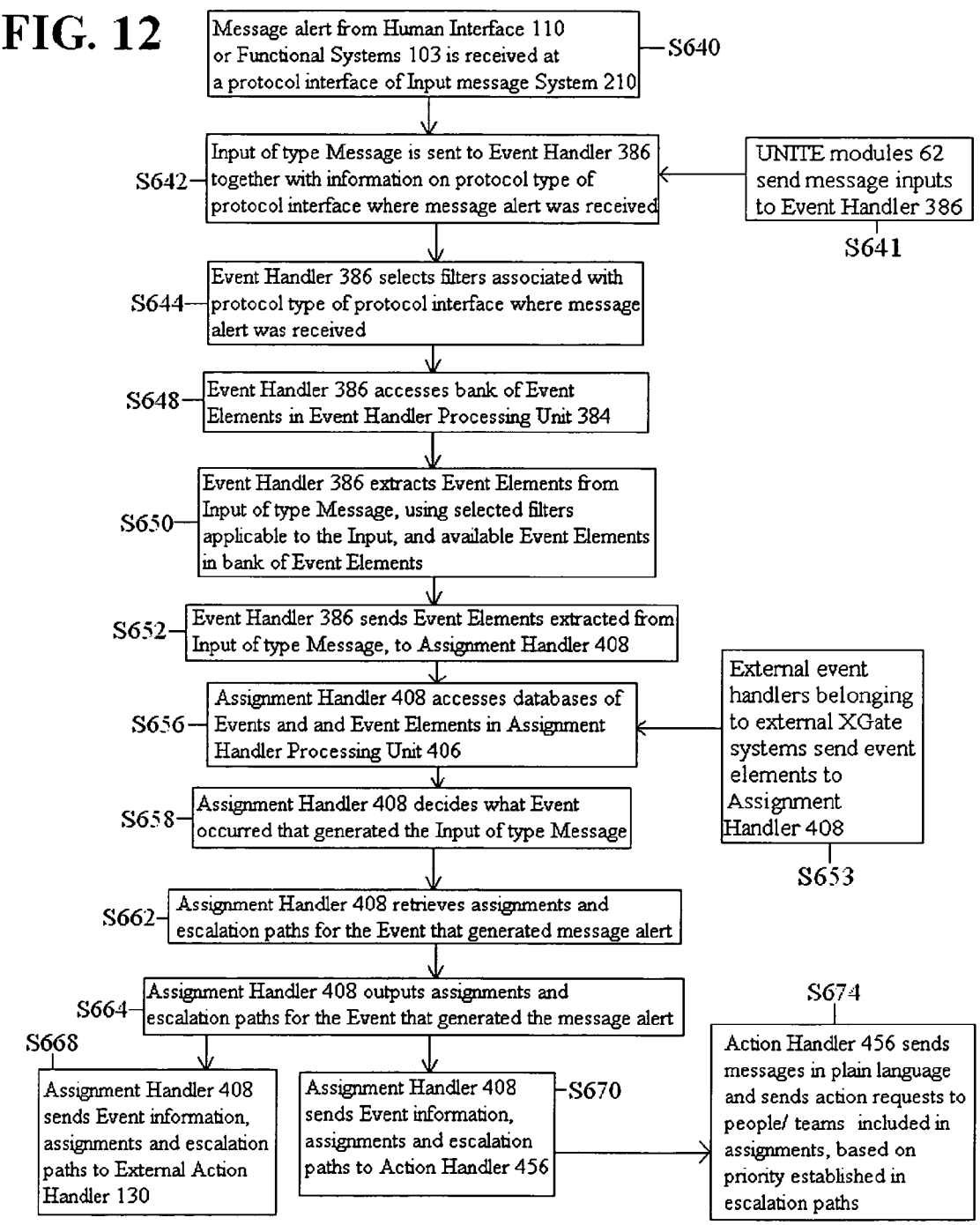
FIG. 12 is a flow diagram illustrating overall operations performed by an automated medical staff assignment system according to an embodiment of the present invention illustrated in FIG. 8.

FIG. 12 is a flow diagram illustrating overall operations performed by an automated medical staff assignment (XGate) system 90 according to an embodiment of the present invention. FIG. 12 illustrates a complete operation mode of XGate system 90 illustrated in FIG. 8.

In general, the XGate system 90 is initially set up by configuring interfaces and ports of input message system 210, setting configurations of XGate system 90 in event handler configuration unit 382, defining events, event elements and assignments of personnel to events in event assignment unit (admin) 402, defining actions for events in action configuration unit (admin) 452, defining users and user teams from among personnel of hospital environment 100 as well as access rights in access rights configuration unit (admin) 475, and setting up user assignment data in duty assignment unit (user) 404.

XGate system 90 handles various types of protocols, in order to get a smart integration with the systems of hospital environment 100. The users of XGate system 90 can create these protocols locally. Another important function of XGate system 90 is that it converts the external events to actions and performs staff assignment. Actions may be paging messages, email messages, UNITE messaging blocks, etc. Other action formats can also be used. XGate system 90 can handle various different types of communication interfaces. XGate system 90 also has complex event handling capabilities. XGate system 90 provides an assignment interface to offer the ability for users to dynamically assign recipients to events. The staff assignment application is an easy to use Graphical Interface that allows a user to assign themselves or others to specific alarms and events, and define escalation paths. The staff assignment application can be used as the single interface for staff assignment on multiple systems.

A message alert from human interface 110 or functional systems 103 is received at a protocol interface of input message system 210 (S640). Consequently, an input of type message is sent to event handler 386 together with information on the protocol type of the protocol interface where the message alert was received (S642). UNITE modules 62 also send message inputs to event handler 386 (S641). Event handler 386 then selects appropriate filters associated with the protocol type of the protocol interface where the message alert was received (S644). A database of event elements is located in event handler processing unit 384. The database of event elements was created using the assignment handler processing unit 406. Event handler 386 accesses the bank of event elements (S648) and extracts event elements from the input of type message, using the selected filters applicable to the input of type message, and available matching event elements located in bank of event elements (S650). Event handler 386 then sends the identified event elements extracted from the input of type message, to assignment handler 408 (S652). External event handlers, which belong to external XGate systems, may also send event elements to assignment handler 408 (S653). Such external event elements are extracted in the external XGate systems from messages received in the external XGate systems.

Databases of events and event elements are located in assignment handler processing unit 406. The database of events was created using data from the action handler processing unit 454, duty assignment unit (user) 404, and event assignment unit (admin) 402. The database of event elements was created using data from the duty assignment unit (user) 404 and event assignment unit (admin) 402. Assignment handler 408 accesses the databases of events and event elements (S656), compares event elements received from event handler 386 against the databases of event and event elements, and decides what event occurred that generated the input of type message (S658).

Assignment handler 408 then retrieves from duty assignment unit (user) 404 and event assignment unit (admin) 402 via assignment handler processing unit 406, assignments and escalation paths for the event that generated the input of type message (S662). Assignment handler 408 then outputs assignments and escalation paths appropriate for the event that generated the message alert (S664). Assignment handler 408 sends the event information, assignments and escalation paths to action handler 456 (S670). Assignment handler 408 may alternatively send the event information, assignments and escalation paths to an external action handler 130 (S668).

Following step S670, action handler 456 creates messages in plain language about the event that generated the message alert, using the event elements, generates action requests for the people/teams included in the event assignments, based on priority established in escalation paths, and then sends the action requests, accompanied by the messages in plain language describing the event, to the appropriate people/teams (S674).

FIG. 13A illustrates a start page for an exemplary implementation of an automated medical staff assignment system according to an embodiment of the present invention. In one implementation, the start page of XGate is an HTML page. The "Duty Assignment" link is a direct link to the duty assignment unit (user) 404. User IDs and passwords are required to access the "Duty Assignment" area. The users of the "Duty Assignment" area are administration, system administration, and predefined users.

The "Administration" area provides access to the event assignment unit (admin) 402, access rights configuration unit (admin) 475 and action configuration unit (admin) 452. The "Administration" area is accessed by administration and system administration using logins and passwords. Upon logging into the "Administration" area, administration personnel can administrate access rights to either the "Administration" area or the "Duty Assignment" area, can configure available events and appropriate actions for events, and can set up indicators for event occurrences.

FIG. 13B illustrates a graphical interface for basic setup of an exemplary implementation of an automated medical staff assignment system according to an embodiment of the present invention. The XGate User Interface includes a Basic Setup area and an Advanced Setup area. The Basic Setup is for configuration and assignments in XGate. The Advanced Setup is for database administration and configuration in XGate.

The graphical interface in FIG. 13B is obtained by clicking on the "Administration" area in FIG. 13A. The "Access Rights" area from FIG. 13A expands into the "User Administration" area in FIG. 13B, where access rights for user teams, such as UNITE user teams, are defined. The "Action Configuration" area from FIG. 13A expands into the "Action Handling" area in FIG. 13B, and corresponds to the action configuration unit (admin) 452. In this area, actions for events are set up, messages transmitted as action requests are defined, and success or failure conditions are input to define when an action was successfully carried out. The "Event Assignment" area from FIG. 13A expands into the "Assignments" area in FIG. 13B, and corresponds to the event assignment unit (admin) 402. In this area, event elements corresponding to events are set up, and addressees for actions are defined. Input data conversions such as translation tables from one language to another can also be set up in the Basic Setup.

Figure 13C:
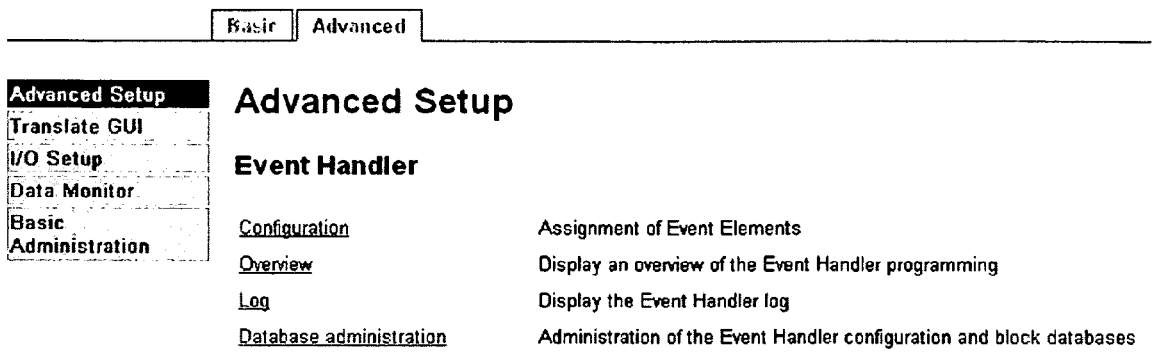
FIG. 13C illustrates a graphical interface for advanced setup of an exemplary implementation of an automated medical staff assignment system according to an embodiment of the present invention.

FIG. 13C illustrates a graphical interface for advanced setup of an exemplary implementation of an automated medical staff assignment system according to an embodiment of the present invention. The advanced setup area is used by engineers and technicians during configuration and database administration in XGate. Using the advanced setup interface illustrated in FIG. 13C it is possible to configure and administrate the XGate system by using the event handler 386 and event handler configuration unit 382, add translations and languages, etc.

Figure 13D:
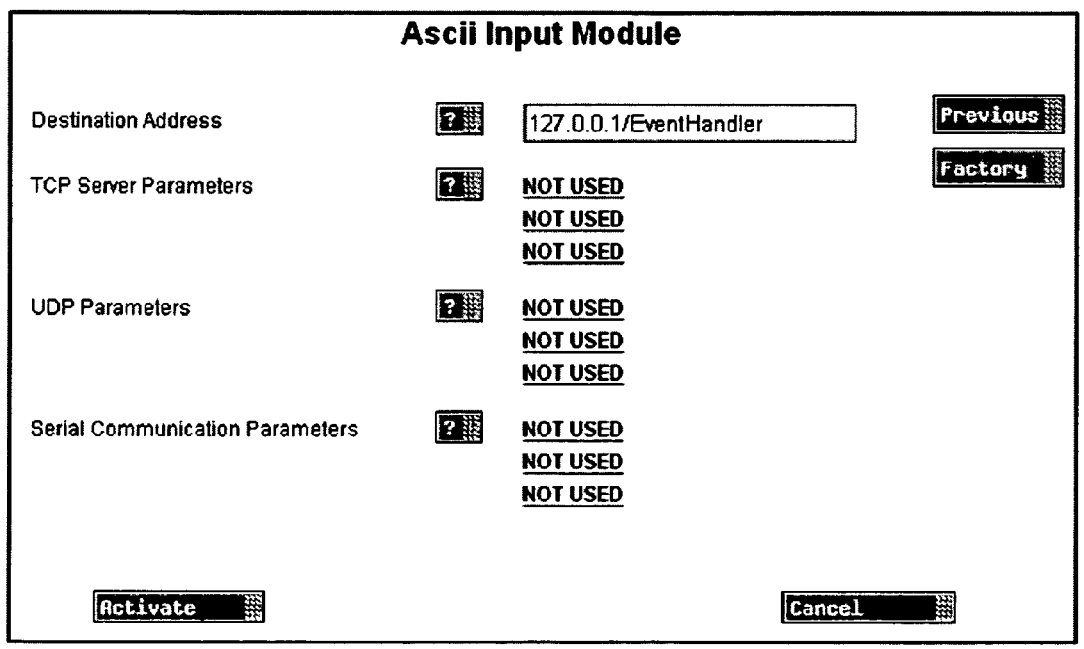
FIG. 13D is a graphical interface for an input message system for an exemplary implementation of an automated medical staff assignment system according to an embodiment of the present invention.

FIG. 13D is a graphical interface for an input message system 210 for an exemplary implementation of an automated medical staff assignment system according to an embodiment of the present invention. FIG. 13D illustrates an ASCII Input Interface that interprets alarm and messages originating in different systems and receives messages via serial ports. The "Destination Address" is a default UNITE address where received input data is sent after being read. The "TCP Server Parameters" area can be set up to include parameters at TCP ports, such as Start/Stop character string, amount of clients that can be connected at the same time, etc. The "UDP Parameters" area can be set up to include parameters at UDP ports. The "Serial Communication Parameters" can be set up to include parameters at RS232/ASCII ports, such as Start/Stop character string, Baud rate, Stop Bits, Parity and Flow Control.

Figure 13E:
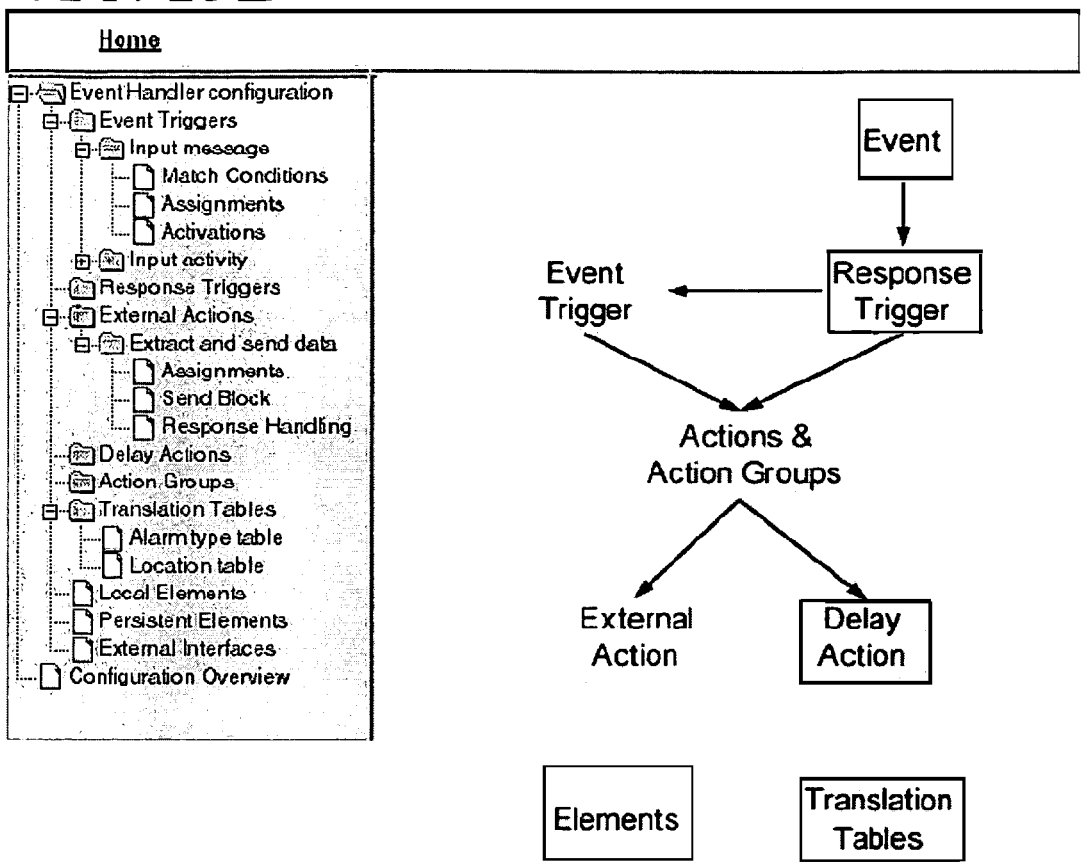
FIG. 13E is a graphical interface for an event handler configuration unit in an exemplary implementation of an automated medical staff assignment system according to an embodiment of the present invention.

FIG. 13E is a graphical interface for an event handler configuration unit 382 in an exemplary implementation of an automated medical staff assignment system according to an embodiment of the present invention. The graphical interface in FIG. 13E illustrates the path of actions in detecting an event, how to extract event information, and how to assign event-related actions to users or teams of users. Event handler configuration unit 382 may be configured for event triggers, response triggers, external actions, translation tables, etc. "Event Triggers" define conditions of incoming events and activate predefined actions for events. "Match Conditions" change states and conditions of triggers when there exists more than one trigger relating to the same event. "External Actions" create event element assignments, by defining, as an example, alarm type, alarm type description, location, location description, etc.

As an example, an input message containing an alarm (03:12345) is received by event handler 386. Event handler 386 extracts the alarm type which is "03", and the location which is "12345". A translation table from event handler configuration unit 382 is used to convert "03" to the meaning of "fire alarm", and the location "12345" to the meaning of "Main building, floor 1".

Figure 13F:
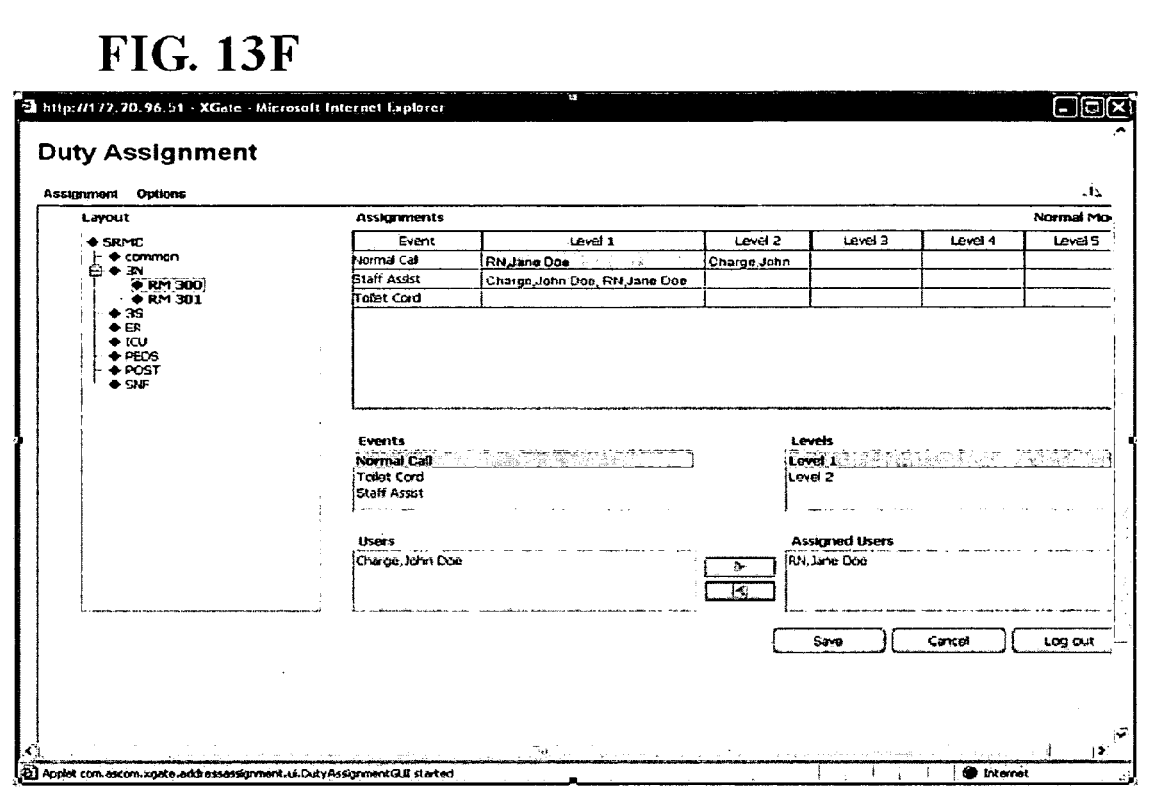

FIG. 13F is a graphical interface for a duty assignment unit (user) 404 in an exemplary implementation of an automated medical staff assignment system according to an embodiment of the present invention. FIG. 13F shows an exemplary interface for the duty assignment unit (user) 404. The duty assignment unit (user) 404 is used to assign users to specific locations and associated events.

The layout box on the left of the screen shot shown of FIG. 13F depicts the configured layout of a facility such as hospital environment or an industrial facility. The layout may include hospital wings or floors as well as sub-categories of rooms. The places written in bold letters are the locations an assigning user has access to, in order to assign appropriate users to locations and their associated events. The accessible locations depend on the user using the duty assignment unit (user) 404. A login and password is required for each user to access the interface shown in FIG. 13F. In FIG. 13F, user assignments are made for location 3N, room 300. Under "Events", the events available for the selected location are listed. In this case the events are Normal Call, Toilet Cord, Staff Assist, for location 3N, room 300. Various locations can have more numbers of events assigned to them. Under "Users", all available users for assignment are listed. There may also be multiple "Levels" of assignments for events. Thus, in case an action text message alert is not completed at the first level, it is then escalated up to a second level, third level, etc., as needed. The events/levels/users are predefined for each location. They have been previously defined by administration using the event assignment unit (admin) 402. Hence, an assigning user using the interface of duty assignment unit (user) 404 can only assign what is available to him or her when he/she logs in. To assign users for the Event "Normal Call" in Room 300, one of "Charge, John Doe" and "RN, Jane Doe" who are working in the current shift and are associated with this type of event, is selected. "RN" is the $1^{st}$ level contact, and "Charge" is the $2^{nd}$ level contact. "RN, Jane Doe" is selected, and her name appears in the "Assignment" menu next to the event name. Hence, Normal Calls from room 300 are assigned to "RN, Jane Doe" as the Level 1 recipient. More than one user can be assigned to an event so that an alert message will go to multiple users when the event occurs. The same user may also be assigned to multiple events. Assignments may be made to more than one location at the same time, such as rooms 300 and 301. Assignments can also be performed from a higher location level. For example, by selecting "3N", assignments can be made for events in all locations under "3N", which means rooms 300 and 301. A notification in the form of a yellow caution triangle appears in the top right-hand side of the screen, if there are events that were left unassigned.

An implementation of XGate system 90 may integrate a plurality of software and hardware tools to provide automatic staff assignment services. XGate system 90 can be used in complex environments such as hospital and industrial environments to perform automated staff assignment to address events occurring in such environments.

Although detailed embodiments and implementations of the present invention have been described above, it should be apparent that various modifications are possible without departing from the spirit and scope of the present invention.

I claim:

1. An apparatus for automated staff assignment in an environment, said apparatus comprising:
   one or more microprocessors coupled to a memory and in communication with one or more computer systems;
   a plurality of communication interfaces associated with different communication protocols and different report formats;
   a message receive system receives a report by way of a communication protocol and in a report format depending on the interface that the report is received, and classifies the report into one of a plurality of report types based on a determination of the report format;
   an event handler configured to recognize event elements in said report by extracting recognizable data from the event elements from the report and searching an event handler database to determine event information categories relative to the extracted event elements, where the extracting of event elements uses an extraction method that is selected based on the report format and communication protocol by which the report is received;
an assignment handler configured to assign duty information for said report, said assignment handler assigning duty information for said report by
determining an event related to said report by searching an assignment database that relates predefined event elements to event meaning and by retrieving an event meaning for said report, and
the assignment handler further assigns staff of said environment to said event based on the determined event and the retrieved duty information associated with the event meaning; and
an action handler configured to compose a message using said event elements and send the message together with action requests to said assigned staff based on the duty information.

2. The apparatus according to claim 1, further comprising:
an event handler configuration unit for generating a configuration and defining filters for a plurality of protocols in order to read reports received by said event handler.

3. The apparatus according to claim 2, wherein said reports are transmitted to said event handler through respective protocols of a plurality of protocols, and upon receiving a report through the respective communications protocol of the plurality of communications protocols, said event handler retrieves a filter associated with the respective protocol by which the report is received from among said generated filters, wherein said filter is used to read said report.

4. The apparatus according to claim 2, further comprising:
an event assignment unit for generating administration-defined event information relating to said plurality of predefined events, and administration-defined staff assignment information for said plurality of predefined staff entities.

5. The apparatus according to claim 4, further comprising:
a duty assignment unit for generating user-defined assignment information using said administration-defined event information relating to said plurality of predefined events, and said administration-defined staff assignment information for said plurality of predefined staff entities.

6. The apparatus according to claim 5, wherein said assignment handler
determines said event related to said report using said administration-defined event information, and
assigns staff of said environment to said event using said administration-defined staff assignment information and said user-defined assignment information.

7. The apparatus according to claim 6, further comprising:
an action configuration unit for generating administration-defined action configurations for said plurality of predefined events.

8. The apparatus according to claim 7, further comprising:
an action handler processing unit functionally connected to said action configuration unit and to said action handler, wherein said action handler processing unit
generates an action message using said event elements of said report and said administration-defined action configurations, and
sends said action message to said action handler for inclusion in said action.

9. The apparatus according to claim 8, further comprising:
an assignment handler processing unit functionally connected to said event assignment unit, said duty assignment unit and said assignment handler, said assignment handler processing unit including said database of predefined event elements.

10. The apparatus according to claim 7, wherein said event assignment unit, said duty assignment unit and said action configuration unit include graphical user interfaces.

11. The apparatus according to claim 5, further comprising:
an access rights unit functionally connected to said duty assignment unit, wherein said access rights unit defines access rights of said staff of said environment.

12. The apparatus according to claim 1, wherein said environment is a hospital environment.

13. The apparatus according to claim 12, wherein
said reports in said hospital environment are transmitted to said event handler using respective communication protocols of said plurality of protocols and said plurality of protocols includes a user datagram protocol (UDP) protocol and a transmission control protocol (TCP) protocol, wherein said UDP protocol has an associated UDP message format and said TCP protocol has an associated TCP message format, and
said event handler receives reports in either of said UDP message format or said TCP message format from integrated messaging system (UNITE) modules of said hospital environment.

14. The apparatus according to claim 1, wherein said assignment handler is functionally connected to an external event handler and an external action handler.

15. A method, performed on an apparatus including one or more microprocessors coupled to a memory and in communication with one or more computer systems, a plurality of communication interfaces associated with different communication protocols and different report formats, an event handler, an assignment handler, and an action handler, of automatically assigning staff in an environment, said event handler capable of recognizing event elements in reports received from said environment for different types of report formats and types of protocols used to send the reports, receiving a report from said environment, each communication interface being configured to receive reports by way of a respective communication protocol and in a report format associated with the protocol, the report format being dictated by the communication protocol, said method comprising:
receiving, by said one or more microprocessors, a report by way of a communication protocol and in a report format depending on the interface that the report is received, and classifying the report into one of a plurality of report types based on a determination of the report format;
recognizing, by said one or more microprocessors, event elements in said report by extracting recognizable data from the event elements from the report and searching an event handler database to determine event information categories relative to the extracted elements, where the extracting of event elements uses an extraction method that is selected based on the report format and communication protocol by which the report is received;
assigning, by said one or more microprocessors, duty information for said report, said step of assigning duty information for said reports including
determining an event related to said report by searching an assignment database that relates predefined event elements to event meaning and retrieving an even meaning for said report, and
further assigning, by said one or more microprocessors, staff of said environment to said event based on the determined event and the retrieved duty information associated with the event meaning; and
composing a message, by said one or more microprocessors, using said event elements and sending the message together with action requests to said assigned staff based on the duty information.

16. The method of automatically assigning staff in an environment as recited in claim 15, wherein said step of assigning, by said assignment handler, information to said reports
   assigns said event to said report from among a plurality of predefined events, and
   assigns staff of said environment to said event from among a plurality of predefined staff entities.

17. The method of automatically assigning staff in an environment as recited in claim 16, further comprising:
   generating, by an event handler configuration unit, a configuration and filters for a plurality of protocols in order to read reports received in said step of extracting event elements from said reports.

18. The method of automatically assigning staff in an environment as recited in claim 17, wherein said report is transmitted through respective protocol of a plurality of protocols, wherein upon receiving the report through the respective protocol of said plurality of protocols, said step of extracting event elements from said reports, by said event handler, retrieves a filter associated with the respective protocol by which the report is received from among said generated filters in order to read said report.

19. The method of automatically assigning staff in an environment as recited in claim 17, further comprising:
   generating, by an event assignment unit, administration-defined event information relating to said plurality of predefined events, and administration-defined staff assignment information for said plurality of predefined staff entities.

20. The method of automatically assigning staff in an environment as recited in claim 19, further comprising:
   generating, by a duty assignment unit, user-defined assignment information using said administration-defined event information relating to said plurality of predefined events, and said administration-defined staff assignment information for said plurality of predefined staff entities.

21. The method of automatically assigning staff in an environment as recited in claim 20, wherein
   said sub-step of determining said event related to said report, by said assignment handler, uses said administration-defined event information, and
   said sub-step of assigning staff of said environment to said event, by said assignment handler, uses said administration-defined staff assignment information and said user-defined assignment information.

22. The method of automatically assigning staff in an environment as recited in claim 21, further comprising:
   generating, by an action configuration unit, administration-defined action configurations for said plurality of predefined events.

23. The method of automatically assigning staff in an environment as recited in claim 22, further comprising:
   generating, by an action handler processing unit, an action message using said event elements of said report and said administration-defined action configurations, and including said action messages in said action for said event.

24. The method of automatically assigning staff in an environment as recited in claim 23, wherein
   said sub-step of determining an event related to said report includes comparing, by an assignment handler processing unit, said event elements with a plurality of predefined event elements.

25. The method of automatically assigning staff in an environment as recited in claim 20, further comprising:
   defining, by an access rights unit, access rights of users for said step of generating user-defined assignment information.

26. The method of automatically assigning staff in an environment as recited in claim 15, wherein said environment is a hospital environment.

27. The method of automatically assigning staff in an environment as recited in claim 26, wherein said step of extracting event elements
   receives, at said event handler, said reports using respective communication protocols of said plurality of protocols, and said plurality of protocols includes a user datagram protocol (UDP) protocol and a transmission control protocol (TCP) protocol, wherein said UDP protocol has an associated UDP message format and said TCP protocol has an associated TCP message format, and
   receives reports in either of said UDP message format or said TCP message format from integrated messaging system (UNITE) modules of said hospital environment.

28. The method of automatically assigning staff in an environment as recited in claim 15, wherein said steps of extracting, by said event handler, recognizable data from event elements from said report in said environment, assigning, by said assignment handler, information for said report, composing, by said action handler, a message, and sending said message to said assigned staff are performed in real-time.

29. The method of automatically assigning staff in an environment as recited in claim 15, wherein said step of sending, by said action handler, said message to said assigned staff
   uses priority information relating to said assigned staff, and generates escalation chains depending on availability of said assigned staff.

30. The method of automatically assigning staff in an environment as recited in claim 15, wherein said step of assigning, by said assignment handler, duty information for said report assigns systems of said environment to said event, and said step of sending, by said action handler, said message sends said message to said assigned systems.

* * * * *